US011427642B2

(12) United States Patent
Trinklein et al.

(10) Patent No.: US 11,427,642 B2
(45) Date of Patent: Aug. 30, 2022

(54) ANTI-BCMA HEAVY CHAIN-ONLY ANTIBODIES

(71) Applicant: TENEOONE, INC., Newark, CA (US)

(72) Inventors: Nathan Trinklein, Newark, CA (US); Shelley Force Aldred, Newark, CA (US); Starlynn Clarke, Newark, CA (US); Wim van Schooten, Newark, CA (US)

(73) Assignee: TENEOONE, INC., Newark, CA (US)

( * ) Notice: Subject to any disclaimer, the term of this patent is extended or adjusted under 35 U.S.C. 154(b) by 110 days.

(21) Appl. No.: 16/622,768

(22) PCT Filed: Jun. 20, 2018

(86) PCT No.: PCT/US2018/038506
§ 371 (c)(1),
(2) Date: Dec. 13, 2019

(87) PCT Pub. No.: WO2018/237006
PCT Pub. Date: Dec. 27, 2018

(65) Prior Publication Data
US 2020/0157232 A1   May 21, 2020

Related U.S. Application Data

(60) Provisional application No. 62/522,295, filed on Jun. 20, 2017.

(51) Int. Cl.
*C07K 16/28* (2006.01)
(52) U.S. Cl.
CPC ...... *C07K 16/2878* (2013.01); *C07K 16/2809* (2013.01); *C07K 2317/21* (2013.01); *C07K 2317/31* (2013.01); *C07K 2317/522* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,500,360 A | 3/1996 | Ahlquist et al. |
| 5,500,362 A | 3/1996 | Robinson et al. |
| 5,585,097 A | 12/1996 | Bolt et al. |
| 5,821,337 A | 10/1998 | Carter et al. |
| 5,929,212 A | 7/1999 | Jolliffe et al. |
| 5,968,509 A | 10/1999 | Gorman et al. |
| 6,706,265 B1 | 3/2004 | Bolt et al. |
| 6,750,325 B1 | 6/2004 | Jolliffe et al. |
| 7,262,276 B2 | 8/2007 | Huang et al. |
| 7,381,803 B1 | 6/2008 | Weiner et al. |
| 7,541,513 B2 | 6/2009 | Bruggemann et al. |
| 7,635,472 B2 | 12/2009 | Kufer et al. |
| 7,728,114 B2 | 6/2010 | Mach et al. |
| 7,862,813 B2 | 1/2011 | Bjork et al. |
| 8,236,308 B2 | 8/2012 | Kischel et al. |
| 8,367,888 B2 | 2/2013 | Bruggemann et al. |
| 8,883,150 B2 | 11/2014 | Craig et al. |
| 9,034,324 B2 | 5/2015 | Kalled et al. |
| 9,365,655 B2 | 6/2016 | Craig et al. |
| 2004/0229310 A1 | 11/2004 | Simmons |
| 2005/0048572 A1 | 3/2005 | Reilly et al. |
| 2007/0065437 A1 | 3/2007 | Elson et al. |
| 2007/0071675 A1 | 3/2007 | Wu et al. |
| 2009/0098134 A1 | 4/2009 | Buelow |
| 2010/0122358 A1 | 5/2010 | Bruggemann et al. |
| 2013/0156769 A1 | 6/2013 | Kufer et al. |
| 2013/0273055 A1 | 10/2013 | Borges et al. |
| 2015/0118251 A1 | 4/2015 | Deslandes |
| 2015/0266966 A1 | 9/2015 | Smith et al. |
| 2015/0368351 A1 | 12/2015 | Vu et al. |
| 2015/0376287 A1 | 12/2015 | Vu et al. |
| 2016/0046724 A1 | 2/2016 | Brogdon et al. |
| 2016/0166689 A1 | 6/2016 | Adler et al. |
| 2016/0194399 A1 | 7/2016 | Irving et al. |
| 2016/0355591 A1 | 12/2016 | Goldenberg et al. |
| 2017/0051068 A1 | 2/2017 | Pillarisetti et al. |
| 2019/0225671 A1 | 7/2019 | van Schooten et al. |
| 2019/0263904 A1 | 8/2019 | Trinklein et al. |
| 2019/0352412 A1 | 11/2019 | Force Aldred et al. |
| 2020/0048348 A1 | 2/2020 | Trinklein et al. |
| 2020/0085839 A1 | 3/2020 | Sidransky et al. |
| 2020/0138865 A1 | 5/2020 | Kochenderfer et al. |

(Continued)

FOREIGN PATENT DOCUMENTS

| | | |
|---|---|---|
| CN | 105384825 | 3/2016 |
| JP | 2001/077342 | 3/2001 |

(Continued)

OTHER PUBLICATIONS

Jiang et al. (J Immunol. Jun. 1, 2011; 186(11): 6136-6147). (Year: 2011).*
Salazar-Camarena et al. (Lupus (2016) 25, 582-592). (Year: 2016).*
Janssens et al., "Generation of Heavy-chain-only Antibodies in Mice," (2006) PNAS 102(41):15130-15135.
Wang et al., "A systematic approach for analysis and characterization of mispairing in bispecific antibodies with asymmetric architecture," (2018) mAbs 10:8, 1226-1235.
Ridgway et al., "'Knobs-into-holes' engineering of antibody CH3 domains for heavy chain heterodimerization," (1996) Protein Eng. 9(7):617-621.
Gupta et al., "Constitutive Inflammatory Cytokine Storm: A Major Threat to Human Health," (2019) Journal of Interferon & Cytokine Research 40(1):19-23.
Crescioli et al., "IgG4 Characteristics and Functions in Cancer Immunity," (2016) Curr Allergy Asthma Rep 16:7.

(Continued)

*Primary Examiner* — Zachary S Skelding
(74) *Attorney, Agent, or Firm* — Jones Day

(57) ABSTRACT

Anti-BCMA heavy chain-only antibodies (UniAb) and disclosed, along with methods of making such antibodies, compositions, including pharmaceutical compositions, comprising such antibodies, and their use to treat B-cell disorders characterized by the expression of BCMA.

13 Claims, 7 Drawing Sheets
Specification includes a Sequence Listing.

(56) References Cited

U.S. PATENT DOCUMENTS

| | | |
|---|---|---|
| 2020/0157232 A1 | 5/2020 | Trinklein et al. |
| 2020/0339685 A1 | 10/2020 | Schellenberger et al. |
| 2021/0047402 A1 | 2/2021 | Trinklein et al. |
| 2021/0095022 A1 | 4/2021 | Aldred et al. |
| 2021/0147564 A1 | 5/2021 | Trinklein et al. |
| 2021/0332133 A1 | 10/2021 | Aldred et al. |
| 2021/0340255 A1 | 11/2021 | Harris et al. |
| 2021/0355215 A1 | 11/2021 | Jorgensen et al. |
| 2021/0388106 A1 | 12/2021 | van Schooten et al. |
| 2021/0403587 A1 | 12/2021 | Buelow et al. |
| 2022/0089729 A1 | 3/2022 | Harris et al. |

FOREIGN PATENT DOCUMENTS

| | | |
|---|---|---|
| JP | 2012504403 | 2/2012 |
| JP | 2013528569 | 7/2013 |
| JP | 2015521032 | 7/2015 |
| RU | 2492186 | 9/2013 |
| RU | 2561457 | 8/2015 |
| WO | 1996/027011 | 9/1993 |
| WO | 1996/027011 | 9/1996 |
| WO | 1996/032478 | 10/1996 |
| WO | 1997/034631 | 9/1997 |
| WO | 1998/050431 | 11/1998 |
| WO | 2001/024811 | 4/2001 |
| WO | 2001/024812 | 4/2001 |
| WO | 2002/066516 | 8/2002 |
| WO | 2006/008548 | 1/2006 |
| WO | 2007/066109 | 6/2007 |
| WO | 2007/117600 | 10/2007 |
| WO | 2009/132058 | 10/2009 |
| WO | 2010/109165 | 9/2010 |
| WO | 2010/109165 A2 | 9/2010 |
| WO | 2011/097603 | 8/2011 |
| WO | 2012/066058 | 5/2012 |
| WO | 2012/122512 | 9/2012 |
| WO | 2012/143498 | 10/2012 |
| WO | 2012/163805 | 12/2012 |
| WO | 2013/072406 | 5/2013 |
| WO | 2013/072415 | 5/2013 |
| WO | 2014/022540 | 2/2014 |
| WO | 2014/047231 | 3/2014 |
| WO | 2014/068079 | 5/2014 |
| WO | 2014/068079 A1 | 5/2014 |
| WO | 2014/089335 | 6/2014 |
| WO | 2014/089335 A2 | 6/2014 |
| WO | 2014/093908 | 6/2014 |
| WO | 2014/122144 | 8/2014 |
| WO | 2015/063339 | 5/2015 |
| WO | 2015/095412 | 6/2015 |
| WO | 2015/121383 | 8/2015 |
| WO | 2015/149077 | 10/2015 |
| WO | 2016/062990 | 4/2016 |
| WO | 2016/079081 | 5/2016 |
| WO | 2016/079177 | 5/2016 |
| WO | 2016/094304 | 6/2016 |
| WO | 2016/113555 | 7/2016 |
| WO | 2016/187546 | 11/2016 |
| WO | 2017/025038 | 2/2017 |
| WO | 2017/025038 A1 | 2/2017 |
| WO | 2017/031104 | 2/2017 |
| WO | 2017/031104 A1 | 2/2017 |
| WO | 2017/081211 | 5/2017 |
| WO | 2017/223111 | 12/2017 |
| WO | 2017/223111 A1 | 12/2017 |
| WO | 2018/039180 | 3/2018 |
| WO | 2018/052503 | 3/2018 |
| WO | 2018/052503 A1 | 3/2018 |
| WO | 2018/083204 | 5/2018 |
| WO | 2018/119215 | 6/2018 |
| WO | 2018/237006 | 12/2018 |
| WO | 2018/237037 | 12/2018 |
| WO | 2019/000223 | 1/2019 |
| WO | 2019/006072 | 1/2019 |
| WO | 2019/126756 | 6/2019 |
| WO | 2019/133761 | 7/2019 |
| WO | 2020/018922 | 1/2020 |
| WO | 2020/087065 | 4/2020 |
| WO | 2020/206330 | 10/2020 |
| WO | 2020/252366 | 12/2020 |
| WO | 2021/127489 | 6/2021 |
| WO | 2021/222578 | 11/2021 |
| WO | 2022/006316 | 1/2022 |

OTHER PUBLICATIONS

Labrijn et al., "Therapeutic IgG4 antibodies engage in Fab-arm exchange with endogenous human IgG4 in vivo," (2009) Nature Biotechnology 27:767-71.

Muyldermans, "Single domain camel antibodies: current status," 2001; Journal of Biotechnology 74(4):277-302.

Revets et al., "Nanobodies as Novel Agents for Cancer Therapy," (2005) Expert Opinion Biological Therapy 5(1):111-124.

Nuttall et al., "Isolation and Characterization of an IgNAR Variable Domain Specific for the Human Mitochondrial Translocase Receptor Tom70," (2003) Eur. J. Biochem. 270:3543-3554.

Nuttall et al., "Selection and Affinity Maturation of IgNAR Variable Domains Targeting Plasmodium falciparum AMA1," (2004) Proteins; Structure, Function and Bioinformatics 55:187-197.

Dooley et al., "Selection and Characterization of Naturally Occuring Single-domain (IgNAR) Antibody Fragments from Immunized Sharks by Phage Display," (2003) Molecular Immunology 40:25-33.

Jaton et al., "Recovery of Antibody Activity Upon Reoxidation of Completely Reduced Polyalanyl Heavy Chain and its Fd Fragment Derived from Anti-2,4-dinitrophenyl Antibody," (1968) Biochemistry 7(12):4185-4195.

Sitia et al., "Developmental Regulation of IgM Secretion: The Role of the Carbosy-terminal Cysteine," (1990) Cell, 60:781-790.

Van der Linden et al., "Comparison of Physical Chemical Properties of Llama $V_{HH}$ Antibody Fragments and Mouse Monoclonal Antibodies," (1999) Biochimica et Biophysica Acta 1431:37-46.

Frenken et al., "Isolation of Antigen Specific Llama $V_{HH}$ Antibody Fragments and Their High Level Secretion by Saccharomyces cerevisiae," (2000) J. Biotechnol. 78:11-21.

Ghahroudi et al., "Selection and Identification of Single Domain Antibody Fragments from Camel Heavy-chain Antibodies," (1997) FEBS Letters 414:521-526.

Nguyen et al., "Heavy-chain only antibodies derived from dromedary are secreted and displayed by mouse B cells," (2003) Immunology; 109(1):93-101.

Bruggemann et al., "Heavy-Chain-Only Antibody Expression and B-Cell Development in the Mouse," (2006) Crit. Rev. Immunol. 26(5):377-90.

Zou et al., "Heavy Chain-Only Antibodies are Spontaneously Produced in Light Chain-Deficient," (2007) J Exp Med 204(13):3271-3283.

Geurts et al., "Knockout Rats via Embryo Microinjection of Zinc-finger Nucleases," (2009) Science 325(5939):433.

Iri-Sofla et al., "Nanobody-based Chimeric Receptor Gene Integration in Jurkat Cells Mediated by PhiC31 Integrase," (2011) Experimental Cell Research 317:2630-2641.

Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386.

Gras et al., "BCMAp: An Integral Membrane Protein in the Golgi Apparatus of Human Mature B Lymphocytes," (1995) International Immunology 7(7):1093-1106.

Tai et al., "Novel Anti-B-Cell Maturation Antigen Antibody-drug Conjugate (GSK2857916) Selectively Induces Killing of Multiple Myeloma," (2014) Blood 123(20):3128-38.

Ali et al., "T Cells Expressing an Anti-B-Cell Maturation Antigen Chimeric Antigen Receptor Cause Remissions of Multiple Myeloma," (2016) Blood 128(13):1688-700.

Kohler et al., "Continuous cultures of fused cells secreting antibody of predefined specificity," (1975) Nature 256:495-497.

(56) References Cited

OTHER PUBLICATIONS

Chothia et al., "Canonical structures for the hypervariable regions of immunoglobulins," (1987) Journal of Molecular Biology 196(4):901-917.
Lefranc et al., "IMGT, the international ImMunoGeneTics database," (1999) Nucleic Acids Research, 27(1):209-212.
Zhao et al., "A germline knowledge based computational approach for determining antibody complementarity determining regions," (2010) Molecular Immunology 47(4):694-700.
Chothia et al., "Conformations of immunoglobulin hypervariable regions," (1989) Nature 342:877-883.
Honegger, "Yet Another numbering scheme for immunoglobulin variable domains: an automatic modeling and analysis tool," (2001) Journal of Molecular Biology 309(3):657-670.
Ofran et al. "Automated identification of complementarity determining regions (CDRs) reveals peculiar characteristics of CDRs and B-cell epitopes," (2008) Journal of Immunology 181(9):6230-6235.
Almagro "Identification of differences in the specificity-determining residues of antibodies that recognize antigens of different size: implications for the rational design of antibody repertoires," (2004) Journal of Molecular Recognition 17(2):132-143.
Padlan et al., "Identification of specificity-determining residues in antibodies," (1995) FASEB Journal 9(1):133-139.
Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Lund et al., "Expression and characterization of truncated forms of humanized L243 IgG1," (2000) European Journal of Biochemistry 267(24):7246-7256.
Boesch et al., "Highly parallel characterization of IgG Fc binding interactions," (2014) MAbs 6(4):915-927.
Chen et al., "Fusion protein linkers: Property, design and functionality," (2013) Advanced Drug Delivery Reviews 65(10): 1357-1369.
Hamers-Casterman et al., "Naturally Occurring Antibodies Devoid of Light Chains," (1993) Letters to Nature 363:446-448.
Desmyter et al., "Antigen Specificity and High Affinity Binding Provided by One Single Loop of a Camel Single-domain Antibody," (2001) Journal of Biological Chemistry 276(28):26285-26290.
Jackson et al., "Driving CAR T-cells Forward," (2016) Nature Reviews Clinical Oncology 13:370-383.
Ravetch et al., "Fc Receptors," (1991) Annual Review of Immunology 9:457-492.
Clynes et al., "Fc Receptors are Required in Passie and Active Immunity to Melanoma," (1998) PNAS (USA) 95(2):652-656.
Gazzano-Santoro et al., "A non-radioactive complement-dependent cytotoxicity assay for anti-CD20 monoclonal antibody," (1996) Journal of Immunological Methods 202(2):163-171.
Concepcion et al., "Label-Free Detection of Biomolecular Interactions Using BioLayer Interferometry for Kinetic Characterization," (2009) Combinatorial Chemistry & High Throughput Screening 12(8):791-800.
Menoret et al., "Characterization of Immunoglobulin Heavy Chain Knockout Rats," (2010) European Journal Immunology 40:2932-2941.
Cui et al., "Targeted Integration in Rat and Mouse Embryos with Zinc-finger Nucleases," (2011) Nature Biotechnology 29(1):64-67.
Carpenter et al., "B-cell Maturation Antigen Is a Promising Target for Adoptive T-cell Therapy of Multiple Myeloma," (2013) Clinical Cancer Research 19(8):2048-2060.
Tai et al., "APRIL and BCMA promote human multiple myeloma growth and immunosuppression in the bone marrow microenvironment," (2016) Blood 127(25):3225-3236.
Sanz et al., "B Cells as Therapeutic Targets in SLE," (2010) Nature Reviews Rheumatology 6:326-337.
Durben et al., "Characterization of a Bispecific FLT3 X CD3 Antibody in an Improved, Recombinant Format for the Treatment of Leukemia," (2015) Molecular Therapy 23(4):648-655.

Mack et al., "A Small Bispecific Antibody Construct Expressed as a Functional Single-chain Molecule with High Tumor Cell Cytotoxicity," (1995) PNAS 92:7021-7025.
Lindhofer et al., "Preferential Species-restricted Heavy/Light Chain Pairing in Rat/Mouse Quadromas. Implications for a Single-step Purification of Bispecific Antibodies," The Journal of Immunology, 155(1): 219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.
Glennie et al., "Preparation and Performance of Bispecific F(ab' gamma)2 Antibody Containing Thioether-linked Fab' gamma Fragments," (1987) Journal of Immunology 139(7): 2367-2375.
Borchmann et al., "Phase 1 trial of the Novel Bispecific Molecule H22xKi-4 in Patients with Refractory Hodgkin Lymphoma," (2002) Blood 100(9):3101-3107.
Adams et al., "Prolonged in Vivo Tumour Retention of a Human Diabody Targeting the Extracellular Domain of Human HER2lneu," (1998) British Journal of Cancer 77(9):1405-1412.
Wu et al., "Simultaneous Targeting of Multiple Disease Mediators by a Dual-variable domain Immunoglobulin," (2007) Nature Biotechnology 25:1290-1297.
Yoon et al., "Both High and Low Avidity Antibodies to the T Cell Receptor can have Agonist Activity," (1994) Immunity 1(7) 563-569.
Baas et al., "Superhuman Mice" (2014) Science-Business eXchange 7(17):1-2.
Trinklein et al., "Abstract LB-090: Sequence-based Discovery of Fully Human Anti-CD3 and Anti-PDL 1 Single Domain Antibodies Using Novel Transgenic Rats," (2016) Cancer Research 76(14 Suppl).
Buelow et al., "Development of a fully human T cell engaging bispecfic antibody for the treatment of multiple myeloma," (2017) J Clin OnCol vol. 35 Supplement.
Dai et al., "Chimeric Antigen Receptors Modified T-cells for Cancer Therapy," (2016) J Natl Cancer Inst 108(7):dvj439.
Hotzel et al., "A strategy for risk mitigation of antibodies with fast clearance," (2012) mABs 4(6)753-760.
Janssens et al., "Generation of Heavy-chain-only Antibodies in Mice," (2006) Proceedings of the National Academy of Sciences of the USA 103(41):15130-15135.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Hipp et al., "A novel BCMA/CD3 bispecific T-cell engager for the treatment of multiple myeloma induces selective lysis in vitro and in vivo," (2017) Nature/Leukemia 31:1743-1751.
Anonymous, "Flow Cytometry Antibody: CD3e Cat. No. CT026-R301, SinoBiological Inc.,—Antibody-Catalogue,": (2017) Sinbiological, Inc. Retrieved from Internet: URL http://www.sinbiologica.com/flow-symmetry-antibody-elite.html.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):396-410.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31 (3):396-410.
Arnett et al., "Crystal Structure of a Human CD3-epsilon/delta Dimer in Complex with a UCHT1 Single-chain Antibody Fragment," (2004) Proc Natl Acad Sci USA 101 (46):16268-16273.
Gershoni et al., "Epitope Mapping—The First Step in Developing Epitope-based Vaccines," (2007) Biodrugs, Adis International, Ltd. NZ 21(3):145-526.
Merchant al., "An Efficient Route to Human Bispecific IgG," (1998) Nature Biotechnology, Gale Group, Inc. 16(7):677-681.
Bruggemann et al., "Human Antibody Production in Transgenic Animals," (2014) Archivum Immunologiae et Therapie Experimentalis, Birkahaeser Verlag AG 63(2):101-108.

(56) References Cited

OTHER PUBLICATIONS

Omniab, "Naturally Optimized Human Antibodies," (Feb. 23, 2016) retrieved from Internet: URL:http://content.stockpr.com/omniab/db/252/746/file/OmniAb.pdf.

Armitage, "A clinical evaluation of the International Lymphoma Study Group classification of non-Hodgkin's lymphoma," (1997) Blood 89(11):3909-3918.

Hanes et al., "New advances in microsphere-based single-dose vaccines," (1997) Advanced Drug Delivery Reviews 28(1):97-119.

Langer, "New Methods of Drug Delivery," (1990) Science 249(4976):1527-1533.

Jemal et al., "Cancer Statistics, 2008," ACS Journals (2008) 58(2):71-96.

Waxman et al., "Racial disparities in incidence and outcome in multiple myeloma: a population-based study," (2010) Blood 116(25):5501-5506.

Pulte et al., "Improvement in Survival of Older Adults with Multiple Myeloma: Results of an Updated Period Analysis of SEER Data," (2011) The Oncologist 16(11):1600-1603.

Kumar et al., "Improved survival in multiple myeloma and the impact of novel therapies," (2008) Blood 111(5):2516-2520.

Tueresson et al., "Patterns of Improved Survival in Patients with Multiple Myeloma in the Twenty-First Century: A Population-Based Study," (2010) Journal of Clinical Oncology 28(5):830-834.

Palumbo et al., "Daratumumab, Bortezomib, and Dexamethasone for Multiple Myeloma," (2016) New England Journal of Medicine 375(8):754-766.

Dimopoulos et al., "Daratumumab, Lenalidomide, and Dexamethasone for Multiple Myeloma," (2016) New England Journal of Medicine 375(14):1319-1331.

Mikkilineni et al., "Chimeric antigen receptor T-cell therapies for multiple myeloma," (2017) Blood 130(24):2594-2602.

Pick et al., "Daratumumab resistance is frequent in advanced-stage multiple myeloma patients irrespective of CD38 expression and is related to dismal prognosis," (2018) European Journal of Haematology 100(5):494-501.

Miller et al., "Design, Construction, and In Vitro Analyses of Multivalent Antibodies," (2003) Journal of Immunology 170(9):4854-4861.

Chen et al., "Fusion protein linkers: Property, design and functionality," (2013) Advanced Health Care Materials 65(10):1357-1369.

Kumar et al., "International Myeloma Working Group consensus criteria for response and minimal residual disease assessment in multiple myeloma," (2016) The Lancet Oncology 17(8):e328-e346.

Gust et al., "Endothelial Activation and Blood-Brain Barrier Disruption in Neurotoxicity after Adoptive Immunotherapy with CD19 CAR-T Cells," (2017) Cancer Discovery 7(12):1405-1419.

Giavridis et al., "CAR T cell-induced cytokine release syndrome is mediated by macrophages and abated by IL-1 blockade," (2018) Nature Medicine 24:731-738.

Norelli et al., "Monocyte-derived IL-1 and IL-6 are differentially required for cytokine-release syndrome and neurotoxicity due to CAR T cells," (2018) Nature Medicine 24:739-748.

Anonymous (TeneoBio, Inc.), "A Study of TNB-383B in Subjects with Relapsed or Refractory Multiple Myeloma," (2019) retrieved from the Internet on May 1, 2019 from URL:https://clinicaltrials.gov/ct2/show/NCT03933735, 4 pages.

Buelow et al., "TNB3838.0001: A Multicenter, Phase 1, Open-Label, Dose-Escalation Andexpansion Study of TNB-3838, a Bispecific Antibodytargeting BCMA in Subjects with Relapsed or Refractorymultiple Myeloma," (2019) Blood 134(Supplement 1):1874.

DiLillo et al., "A BCMAxCD3 Bispecifi T Cell-engaging Antibody Demontstrates Robust Antitumor Efficacy Similar to that of Anti-BCMA CAR T Cells," (2020) Blood Advances 5(5):1291-1304.

Rodriguez et al., "Paper: Initial Results of a Phase 1 Study of TNB-383B, a BCMA x CD3 Bispecific T-cell Redirecting Antibody in Relapsed/Refractory Multiple Myeloma," (2020) retrieved from the Internet at URL:https//ash.confex.com/ash/2020/webprogram/Paper139893.html.

Alderson et al., "CAT-8015: A Second-Generation Pseudomonas Exotoxin A-Based Immunotherapy Targeting CD22-Expressing Hematologic Malignancies," (2009) Clinical Cancer Research 15(3):832-839.

"Antibody Therapeutics—Teneobio's Next Generation of Multispecific Antibody Therapuetics," Jan. 1, 2018 retrieved from the Internet URL:https://drug-dev.com/antibody-therapeutics-teneobios-next-generation-of-multispecific-antibody-therapeutics/.

Armour et al., "Recombinant human IgG molecules lacking Fcγ receptor I binding and monocyte triggering activities," (1999) Eur J Immunol. 29(8):2613-2624.

Buelow et al., "Meeting Info: 2018 ASCO-SITC Clinical Immuno-Oncology Symposium," (2018) Journal of Clinical Oncology 36(5):60.

Buelow et al., "Meeting Info: 61st Annual Meeting of the American Society of Hematology," (2019) 134(1):1874.

Business Wire: "OMT Therapeutics Announces UniRat™ Alliance with Caltech," May 15, 2015 retrieved from the Internet: URL:https://www.businesswire.com/news/home/20150514006523/en/OMT-Therapeutics-Announces-UniRat™—Alliance-Caltech.

Canfield et al "The Binding Affinity of Human IgG for its High Affinity Fc Receptor Is Determined by Multiple Amino Acids in the CH2 Domain and Is Modulated by the Hinge Region," (1991) J. Exp. Med. 173:1483-1491.

Caraccio et al., "Bispecific Antibodies for Multiple Myeloma: A Review of Targets, Drugs, Clinical Trials and Future Directions," (2020) Frontiers in Immunology 11(50):1-25.

Chassaing et al., "Dextran Sulfate Sodium (DSS)-Inducted Colitis in Mice," (2014) Current Protocols in Immunology 15(25):1-14.

Chini et al., "The Pharmacology of CD38/NADase: An Emerging Target in Cancer and Dieseases of Aging," (2018) Trends in Pharmacological Sciences 39(4):424-436.

Chou et al., "Quantitative Analysis of Dose-Effect Relationships: The Combined Effects of Multiple Drugs or Enzyme Inhibitors," (1984) Hopkins University School of Medicine 22:27-55.

Christian et al., "Measuring Bacterial Ectoenzyme Activities in Marine Waters Using Mercuric Chloride as a Preservative and Control," (1995) Marine Ecology Progress Series 123:217-224.

DaSilva, "Abstract 34: A MET x MET bispecific antibody that induces receptor degradation potently inhibits the growth of MET-addicted tumor xenografts," (2017) AACR Annual Meeting 1-2.

Dondelinger et al., "Understanding the Significance and Implications of Antibody Numbering and Antigen-Binding Surface/Residue Definition," (2018) Front. Immunol. 9(2278):1-15.

Duncan et al., "Localization of the binding site for the human high-affinity Fc receptor on IgG," (1988) Nature 332:563-564.

Force Aldred et al., "Winning the Numbers Game: Novel Multispecific Therapeutics from a Diverse Collection of Human Domain Antibodies," (Oct. 10, 2016), retrieved from the Internet URL: https://2019.lakepharma.com/files/symposiums/Winning%20the%20Numbers%20Game%20-%20Novel%20Multi-specific%20Therapeutics%20from%20a%20Diverse%20Collection%20of%20Human%20Domain%20Antibodies%20-%20Shelley%20Force%20Aldred.pdf.

Fry et al., "CD22-targeted CAR T Cells Induce Remission in B-ALL that is Naïve or Resistant to CD19-targeted CAR Immunotherapy," (2018) Nature Medicine 24(1):20-28.

Haffner et al., "Discovery, Synthesis, and Biological Evaluation of Thiazoloquin(az)olin(on)es as Potent CD38 Inhibitors," (2015) Journal of Medical Chemistry 58:3548-3571.

Hamilton et al., "Humanization of Yeast to Produce Complex Terminally Sialylated Glycoproteins," (2006) Science 313(5792):1441-1443.

Hlavacek et al., "Steric Effects on Multivalent Ligand-Receptor Binding: Exclusion of Ligand Sites by Bound Cell Surface Receptors," (1999) Biophysical Journal 76(6):3031-3043.

Jabbour et al., "Monoclonal Antibodies in Acute Lymphoblastic Leukemia," (2015) Blood 125(26):2010-2016.

Kanda et al., "Establishment of a GDP-mannose 4,6-dehydratase (GMD) knockout host cell line: A new strategy for generating completely non-fucosylated recombinant therapeutics," (2007) Journal of Biotechnology 139:300-310.

(56) References Cited

OTHER PUBLICATIONS

Kaneko et al., "Anti-Inflammatory Activity of Immunoglobulin G Resulting from Fc Sialylation," (2006) Science 313(5787):670-673.
Lefranc et al., "The Immunoglobulin FactsBook," (2001) Academic Press, FactsBook Series, pp. 1-240.
Mariuzza et al., "The Structural Basis of Antigen-antibody Recognition," (1987) Ann Rev Biophys, Biophys Chem 16:139-159.
Menoret et al., "Transgenic Animals and Genetic Engineering Techniques," (2015) Transgenic Res 24:1079-1085.
Nishimoto et al., "Adoptive Therapy with Cord Blood T Regulatory Cells Enhances Anti-Myeloma Efficacy of T Cell Based Immunotherapies," (2020) Blood, vol. 136 Blood, Supplement 1, 2020, pp. 26-27.
Nguyen et al., "Functional Heavy-Chain Antibodies in Camelidae," (2001) Advances in Immunology 79:261-296.
Plückthun et al., "New protein engineering approaches to multivalent and bispecific antibody fragments," (1997) Immunology 3(2):83-105.
Presta et al., "Generation of a Humanized, High Affinity Anti-tissue Factor Antibody for Use as a Novel Antithrombotic Therapeutic," (2001) Thromb Haemost 85:379-389.
Presta et al., "Humanization of an antibody directed against IgE," (1993) Journal of Immunology 151:2623-2632.
Pulte et al., "CD39 Expression on T Lymphocytes Correlates with Severity of Disease in Patients With Chronic Lymphocytic Leukemia," (2011) Clinical Lymphoma, Myeloma & Leukemia 11(4):367-372.
Qin et al., "Paralleled comparison of vectors for the generation of CAR-T cells," (2016) Anti-Cancer Drugs 27(8):711-722.
Rangaswamy et al., "A Novel T-cell Bispecific Antibody Platform for Efficient T-cell Mediated Killing of Tumor Cells with Minimal Cytokine Release," (2018) Journal of Clinical Oncology 36(5):Supplement 209.
Revets et al., "Nanobodies as novel agents for cancer therapy," (2005) Expert Opin Biol Ther 5(1):111-124.
Rouet et al., "Fully Human VH Single Domains That Rival the Stability and Cleft Recognition of Camelid Antibodies," (2015) Journal of Biological Chemistry 290(19):11905-11917.
Ryan et al., "Antibody Targeting of B-cell Maturation Antigen on Malignant Plasma Cells," (2007) Molecular Cancer Therapeutics 6(11):3009-3018.
Shallis et al., "The multi-faced potential of CD38 antibody targeting in multiple myeloma," (2017) Cancer Immunol Immunother 66:697-703.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.
Shoji-Hosaka et al., "Enhanced Fc-Dependent Cellular Cytotoxicity of Fc Fusion Proteins Derived from TNF Receptor II and LFA-3 by Fucose Removal from Asn-Linked Oligosaccharides," (2006) Journal of Biochemistry 140:777-783.
Tao et al., "Structural features of human immunoglobulin G that determine isotype-specific differences in complement activation," (1993) Journal of Experimental Medicine 178(2):661-667.
Trinklein et al., "Efficient tumor killing and minimal cytokine release with novel T-cell agonist bispecific antibodies," (2019) MABS 11(4):639-652.
Van Schooten et al., "A novel CD3/BCMA bispecific antibody selectively kills plasma cells in bone marrow of healthy individuals with improved safety," (2019) Lupus Science & Medicine 6, Abstract 293.
Walker et al., "CD22: An Inhibitory Enigma," (2007) Immunology 123:314-325.
Weidle et al., "The Intriguing Options of Multispecific Antibody Formats for Treatment of Cancer," (2013) Cancer Genomics & Proteomics 10(1):1-18.
Werther et al., "Humanization of an anti-lymphocyte function-associated antigen (LFA)-1 monoclonal antibody and reengineering of the humanized antibody for binding to rhesus LFA-1," (1996) Journal of immunology 157:4986-4995.
Wu et al., "CD38-expressing macrophages drive age-related NAD+ decline," (2020) Nature Metabolism 2:1186-1187.
U.S. Appl. No. 16/472,173, filed Jun. 20, 2019, 2019/0352412 (Nov. 21, 2019), TeneoBio, Inc., Anti-BCMA Heavy Chain-Only Antibodies, Pending.
U.S. Appl. No. 16/622,881, filed Dec. 13, 2019, 2021/0147564 (May 20, 2021), TeneoBio, Inc., Anti-BCMA Heavy Chain-Only Antibodies, Pending.
U.S. Appl. No. 16/312,743, filed Jun. 20, 2017, 2019/0263904 (Aug. 29, 2019), TeneoBio, Inc., CD3 Binding Antibodies, Pending.
U.S. Appl. No. 16/332,665, filed Mar. 12, 2019, 2020/0048348 (Feb. 13, 2020), TeneoBio, Inc., CD3 Binding Antibodies, Pending/Allowed.
U.S. Appl. No. 17/492,444, filed Oct. 1, 2021, 2022/0025047 (Jan. 27, 2021), TeneoOne, Inc., CD3 Binding Antibodies, Pending.
U.S. Appl. No. 17/308,946, filed May 5, 2021, 2021/0340255 (Nov. 4, 2021), TeneoOne, Inc., Multispecific Heavy Chain Antibodies With Modified Heavy Chain Constant Regions, Patented U.S. Pat. No. 11,186,639 (Nov. 30, 2021).
U.S. Appl. No. 17/347,553, filed Jun. 14, 2021, 2022/0089729 (Mar. 24, 2022), TeneoTwo, Inc., Multispecific Heavy Chain Antibodies With Modified Heavy Chain Constant Regions, Pending/Allowed.
U.S. Appl. No. 17/533,957, filed Nov. 23, 2021, Not Yet Published, TeneoOne, Inc., Multispecific Heavy Chain Antibodies With Modified Heavy Chain Constant Regions, Pending.
U.S. Appl. No. 16/958,105, filed Dec. 27, 2018, 2020/0339685 (Oct. 29, 2020), TeneoBio, Inc., CD3-Delta/Epsilon Heterodimer Specific Antibodies, Pending.
U.S. Appl. No. 16/327,299, filed Aug. 22, 2017, 2019/0225671 (Jul. 25, 2019), TeneoBio, Inc., Transgenic Non-Human Animals Producing Modified Heavy Chain-Only Antibodies, Pending.
U.S. Appl. No. 17/278,268, filed Sep. 20, 2019, 2021/0355215 (Nov. 18, 2021), TeneoBio, Inc., Methods For Purifying Heterodimeric, Multispecific Antibodies, Pending.
U.S. Appl. No. 17/244,785, filed Apr. 29, 2021, 2021/0403587 (Dec. 30, 2021), TeneoOne, Inc., Methods Of Treating Multiple Myeloma, Pending.
U.S. Appl. No. 16/626,991, filed Dec. 27, 2019, 2020/0138865 (May 7, 2020), The United States of America, as represented by the Secretary, Department of Health and Human Services, Bethesda, MD (US); and TeneoBio, Inc., Anti-B-Cell Maturation Antigen Chimeric Antigen Receptors With Human Domains, Pending.
U.S. Appl. No. 16/956,502, filed Jun. 19, 2020, 2021/0095022 (Apr. 1, 2021), TeneoBio, Inc., Heavy Chain Antibodies Binding to CD22, Pending.
U.S. Appl. No. 17/288,485, filed Apr. 23, 2021, 2021/0388106 (Dec. 16, 2021), TeneoBio, Inc., Heavy Chain Antibodies Binding to CD38, Pending.
U.S. Appl. No. 17/260,213, filed Jan. 13, 2021, 2021/0332133 (Oct. 28, 2021), TeneoBio, Inc., Heavy Chain Antibodies Binding to CD19, Pending.
U.S. Appl. No. 17/601,417, filed Oct. 4, 2021, Not Yet Published, TeneoBio, Inc., Heavy Chain Antibodies Binding to PSMA, Pending.
U.S. Appl. No. 16/900,586, filed Jun. 12, 2020, 2021/0047402 (Feb. 18, 2021), TeneoBio, Inc., Multispecific Heavy Chain Antibodies Binding to CD22 and CD3, Pending.

\* cited by examiner

| CLONE ID | seq_aa_CDR1 | seq_aa_CDR2 | seq_aa_CDR3 |
|---|---|---|---|
| 308636 | GFTVSSYG (SEQ ID NO: 1) | IRGSDGST (SEQ ID NO: 8) | AKQGGNDGPFDY (SEQ ID NO: 12) |
| 308837 | GFTVSSYG (SEQ ID NO: 1) | IRGSDGST (SEQ ID NO: 8) | AKQGGNDGPFDY (SEQ ID NO: 12) |
| 308912 | GFTVSSYG (SEQ ID NO: 1) | IRGSDGST (SEQ ID NO: 8) | AKQGGNDGPFDY (SEQ ID NO: 12) |
| 314309 | GFTISSYG (SEQ ID NO: 2) | IRGSDGTT (SEQ ID NO: 9) | AKQGGNDGPFDY (SEQ ID NO: 12) |
| 314341 | GFTVSSYG (SEQ ID NO: 1) | IRGSDGST (SEQ ID NO: 8) | AKQGGNDGPFDY (SEQ ID NO: 12) |
| 314344 | GFTVSSYG (SEQ ID NO: 1) | IRGSDGST (SEQ ID NO: 8) | AKQGGNDGPFDY (SEQ ID NO: 12) |
| 314359 | GFTVSSYG (SEQ ID NO: 1) | IRGSDGST (SEQ ID NO: 8) | AKQGGNDGPFDY (SEQ ID NO: 12) |
| 314362 | GFTVSSYG (SEQ ID NO: 1) | IRGSDGST (SEQ ID NO: 8) | AKQGGNDGPFDY (SEQ ID NO: 12) |
| 314364 | GFTVSSYG (SEQ ID NO: 1) | IRGSDGST (SEQ ID NO: 8) | AKQGGNDGPFDY (SEQ ID NO: 12) |
| 314404 | GFTISSYG (SEQ ID NO: 2) | IRGSDGST (SEQ ID NO: 8) | AKQGGNDGPFDY (SEQ ID NO: 12) |
| 314407 | GFTVSSYG (SEQ ID NO: 1) | IRGSDGTT (SEQ ID NO: 9) | AKQGGNDGPFDY (SEQ ID NO: 12) |
| 314422 | GFTVSSYG (SEQ ID NO: 1) | IRGSDGTT (SEQ ID NO: 9) | AKQGGNDGPFDY (SEQ ID NO: 12) |
| 314433 | GFTITSYG (SEQ ID NO: 3) | IRGSDGST (SEQ ID NO: 8) | AKQGGNDGPFDY (SEQ ID NO: 12) |
| 314481 | GFTVSSYG (SEQ ID NO: 1) | IRGSDGTT (SEQ ID NO: 9) | AKQGGNDGPFDY (SEQ ID NO: 12) |
| 308806 | GFTISSYG (SEQ ID NO: 2) | IRGSDGTT (SEQ ID NO: 9) | AKQGGNDGPFDH (SEQ ID NO: 13) |
| 314451 | GFTVSSYG (SEQ ID NO: 1) | IRGSDGST (SEQ ID NO: 8) | AKQGGNDGPFDH (SEQ ID NO: 13) |
| 314457 | GFTISSYG (SEQ ID NO: 2) | IRGSDGST (SEQ ID NO: 8) | AKQGGNDGPFDH (SEQ ID NO: 13) |
| 314474 | GFNVSSYG (SEQ ID NO: 4) | IRGSDGST (SEQ ID NO: 8) | AKQGGNDGPFDH (SEQ ID NO: 13) |
| 308902 | GFTVSSYG (SEQ ID NO: 1) | IRGSDGST (SEQ ID NO: 8) | AKQGENDGPFDY (SEQ ID NO: 14) |
| 314444 | GFTISNYG (SEQ ID NO: 5) | IRGSDGST (SEQ ID NO: 8) | AKQGENDGPFDH (SEQ ID NO: 14) |
| 314453 | GFTISSYG (SEQ ID NO: 2) | IRGSDGTT (SEQ ID NO: 9) | AKQGENDGPFDH (SEQ ID NO: 14) |
| 314473 | GFTISSYG (SEQ ID NO: 2) | IRGSDGTT (SEQ ID NO: 9) | AKQGENDGPFDH (SEQ ID NO: 14) |
| 308635 | GFTVSSYG (SEQ ID NO: 1) | IRGSDGST (SEQ ID NO: 8) | AKQGENDGPFDY (SEQ ID NO: 15) |
| 308731 | GFTFSSSA (SEQ ID NO: 6) | ISGSGDTT (SEQ ID NO: 10) | AKQGENDGPFDY (SEQ ID NO: 15) |
| 314322 | GFTISSYG (SEQ ID NO: 2) | IRGSDGTT (SEQ ID NO: 9) | AKQGENDGPFDY (SEQ ID NO: 15) |
| 314327 | GFTVSSYG (SEQ ID NO: 1) | IRGSDGST (SEQ ID NO: 8) | AKQGENDGPFDY (SEQ ID NO: 15) |
| 314381 | GFTVSSYG (SEQ ID NO: 1) | IRGSDGST (SEQ ID NO: 8) | AKQGENDGPFDY (SEQ ID NO: 15) |
| 314383 | GFTVSSYG (SEQ ID NO: 1) | IRGSDGST (SEQ ID NO: 8) | AKQGENDGPFDY (SEQ ID NO: 15) |

FIG. 1

| 314390 | GFTISSYG (SEQ ID NO: 2) | IRGSDGTT (SEQ ID NO: 9) | AKQGENDGPFDY (SEQ ID NO: 15) |
| --- | --- | --- | --- |
| 314403 | GFTISSYG (SEQ ID NO: 2) | IRGSDGTT (SEQ ID NO: 9) | AKQGENDGPFDY (SEQ ID NO: 15) |
| 314434 | GFTVSSYG (SEQ ID NO: 1) | IRGSDGST (SEQ ID NO: 8) | AKQGENDGPFDY (SEQ ID NO: 15) |
| 314477 | GINFSSYA (SEQ ID NO: 7) | ISGDSGNT (SEQ ID NO: 11) | AKQGENDGPFDY (SEQ ID NO: 15) |
| 314480 | GFTVSSYG (SEQ ID NO: 1) | IRGSDGST (SEQ ID NO: 8) | AKQGENDGPFDY (SEQ ID NO: 15) |
| 314486 | GFTVSSYG (SEQ ID NO: 1) | IRGSDGST (SEQ ID NO: 8) | AKQGENDGPFDY (SEQ ID NO: 15) |
| 314488 | GFTVSSYG (SEQ ID NO: 1) | IRGSDGST (SEQ ID NO: 8) | AKQGENDGPFDY (SEQ ID NO: 15) |

FIG. 1, cont.

| CLONE ID | seq_aa_FR1_FR4 |
|---|---|
| 308636 | EVQVLESGGGLVQPGGSLRLSCAASGFTVSSYGMSWVRQPPGKGMEWVSGIRGSDGSTFYADSVKGRFTISRDNATNTLYLQMNSLRAEDTAVYYCAKQGGNDGPFDYRGQGTLVTVSS (SEQ ID NO: 16) |
| 308837 | EVQLLESGGGLVQPGGSLRLSCAASGFTVSSYGMSWVRQAPGKGPEWVSGIRGSDGSTYYADSVKGRFTISRDNATNTLYLQMNSLRAEDTAVYYCAKQGGNDGPFDYRGQGTLVTVSS (SEQ ID NO: 17) |
| 308912 | EVQLLESGGGLVQPGGSLRLSCAASGFTVSSYGMSWVRQPPGKGMEWVSGIRGSDGSTYYADSVKGRFTISRDNAKNTLYLQMNSLRAEDTAVYYCAKQGGNDGPFDYRGQGTLVTVSS (SEQ ID NO: 18) |
| 314309 | EVQLLESGGGLVQPGGSLRLSCAASGFTISSYGMSWVRQAPGKGVEWVSGIRGSDGTTYYADSVKGRFTISRDNSRNTLYLQMNSLRAEDTAVYYCAKQGGNDGPFDYRGQGTLVTVSS (SEQ ID NO: 19) |
| 314341 | EVQLLESGGGLVQPGGSLRLSCAASGFTVSSYGMSWVRQPPGKGMEWVSGIRGSDGSTFYADSVKGRFTISRDNSRNTLYLQMNSLRAEDTAVYYCAKQGGNDGPFDYRGQGTLVTVSS (SEQ ID NO: 20) |
| 314344 | EVQLLESGGGLVQPGGSLRLSCAASGFTVSSYGMSWVRQPPGKGMEWVSGIRGSDGSTFYADSVKGRFTISRDNAKNTLYLQMNSLRAEDTAVYYCAKQGGNDGPFDYRGQGTLVTVSS SEQ ID NO: 21) |
| 314359 | EVQLLESGGGLVQAGGSLRLSCAASGFTVSSYGMSWVRQPPGKGMEWVSGIRGSDGSTYYADSVKGRFTISRDNAKNTLYLQMNSLRAEDTAVYYCAKQGGNDGPFDYRGQGTLVTVSS (SEQ ID NO: 22) |
| 314362 | EVQLLESGGGLVQPGGSLRLSCAASGFTVSSYGMSWVRQAPGKGPEWVSGIRGSDGSTYYADSVKGRFTISRDNAKNTLYLQMNSLRAEDTAVYYCAKQGGNDGPFDYRGQGTLVTVSS (SEQ ID NO: 23) |
| 314364 | EVQLLESGGGLVQAGGSLRLSCAASGFTVSSYGMSWVRQAPGKGVEWVSGIRGSDGTTYYADSVKGRFTISRDNSKNTLYLQMNSLRAEDTAVYYCAKQGGNDGPFDYRGQGTLVTVSS (SEQ ID NO: 24) |
| 314404 | EVQLLESGGGLVQPGGSLRLSCAASGFTVSSYGMSWVRQAPGKGPEWVSGIRGSDGSTYYADSVKGRFTISRDNSRNTLYLQMNSLRAEDTAVYYCAKQGGNDGPFDYRGQGTLVTVSS (SEQ ID NO: 25) |
| 314407 | EVQLLESGGDLVQSGGSLRLSCAASGFTVSSYGMSWVRQAPGKGPEWVSGIRGSDGTTYYADSVKGRFTISRDSSRNTLYLQMNSLRAEDTAVYYCAKQGGNDGPFDYRGQGTLVTVSS (SEQ ID NO: 26) |
| 314422 | EVQLLESGGGLVQPGGSLRLSCAASGFTISSYGMSWVRQAPGKGPEWVSGIRGSDGTTYYADSVKGRFTISRDNSKNTLYLQMNSLRAEDTAVYYCAKQGGNDGPFDYRGQGTLVTVSS (SEQ ID NO: 27) |
| 314433 | EVQLLESGGDLVQPGGSLRLSCAASGFTISSYGMSWVRQAPGKGVEWVSGIRGSDGTTYYADSVKGRFTISRDSSRNTLYLQMNSLRAEDTAVYYCAKQGGNDGPFDYRGQGTLVTVSS (SEQ ID NO: 28) |
| 314481 | EVQLLESGGGLVQPGGSLRLSCAASGFTVSSYGMSWVRQAPGKGPEWVSGIRGSDGSTFYADSVKGRFTISRDNAKNTLFLQMNSLRAEDTAVYYCAKQGGNDGPFDYRGQGTLVTVSS (SEQ ID NO: 29) |
| 308806 | EVQLLESGGGLVQPGGSLRLSCAASGFTISSYGMSWVRQAPGKGVEWVSGIRGSDGTTYYADSVKGRFTISRDSSRNTLYLQMNSLRAEDTAVYYCAKQGGNDGPFDHRGQGTLVTVSS (SEQ ID NO: 30) |
| 314451 | EVQLLESGGGLVQPGGSLRLSCAASGFTVSSYGMSWVRQPPGKGMEWVSGIRGSDGSTYYADSVKGRFTISRDNATNTLYLQMNSLRAEDTAVYYCAKQGGNDGPFDHRGQGTLVTVSS (SEQ ID NO: 31) |
| 314457 | EVQLLESGGGLVQPGGSLRLSCAASGFTVSSYGMSWVRQPPGKGMEWVSGIRGSDGSTYYADSVKGRFTISRDNAKNTLYLQMNSLRAEDTAVYYCAKQGGNDGPFDHRGQGTLVTVSS (SEQ ID NO: 32) |

FIG. 2

| | |
|---|---|
| 314474 | EVQLLESGGGLVQPGGSLRLSCAASGFNVSSYGMSWVRQPPGKGMEWVSGIRGSDGSTYYADSVKGRFTISRDNAKNTLYLQMNSLRAE DTAVYYCAKQGGNDGPFDHRGQGTLVTVSS (SEQ ID NO: 33) |
| 308902 | EVQLLESGGGLVQPGGSLRLSCAASGFTVSSYGMSWVRQAPGKGPEWVSGIRGSDGSTYYADSVKGRFTISRDNSKNTLYLQMNSLRAE DTAVYYCAKQGENDGPFDHRGQGTLVTVSS (SEQ ID NO: 34) |
| 314444 | EVQLLESGGGLVQAGGSLRLSCAASGFTVSNYGMSWVRQAPGKGPEWVSGIRGSDGSTYYADSVKGRFTISRDNSKNTLYLQMNSLRAE DTAVYYCAKQGENDGPFDHRGQGTLVTVSS (SEQ ID NO: 35) |
| 314453 | EVQLLESGGGLVQPGGSLRLSCAASGFTISSYGMSWVRQAPGKGPEWVSGIRGSDGTTYYADSVKGRFTISRDNSRNTLHLQMNSLRAE DTAVYYCAKQGENDGPFDHRGQGTLVTVSS (SEQ ID NO: 36) |
| 314473 | EVQLLESGGGLVQPGGSLRLSCAASGFTISSYGMSWVRQAPGKGVEWVSGIRGSDGTTYYADSVKGRFTISRDNSRNTLYLQMNSLRAE DTAVYHCAKQGENDGPFDHRGQGTLVTVSS (SEQ ID NO: 37) |
| 308635 | EVQLLESGGGLVQAGGSLRLSCAASGFTVSSYGMSWVRQAPGKGPEWVSGIRGSDGSTYYADSVKGRFTISRDNSKNTLYLQMNSLRAE DTAVYHCAKQGENDGPFDYRGQGTLVTVSS (SEQ ID NO: 38) |
| 308731 | EVQLLESGGGLVQPGGSLRLSCAASGFTFSSSAMSWVRQPPGKGLEWVSVISGSGDTTYYADSVKGRFTISRDNSRNTLHLQMNSLRAE DTAVYHCAKQGENDGPFDYRGQGTLVTVSS (SEQ ID NO: 39) |
| 314322 | EVQLLESGGGLVQPGGSLRLSCAASGFTISSYGMSWVRQAPGKGPEWVSGIRGSDGSTYYADSVKGRFTISRDNSKNTLYLQMNSLRAE DTAVYHCAKQGENDGPFDYRGQGTLVTVSS (SEQ ID NO: 40) |
| 314327 | EVQLLESGGGLVQPGGSLRLSCAASGFTVSSYGMSWVRQAPGKGPEWVSGIRGSDGSTFYADSVKGRFTISRDNSKNTLYLQMNSLRAE DTAVYHCAKQGENDGPFDYRGQGTLVTVSS (SEQ ID NO: 41) |
| 314381 | EVQVLESGGGLVQPGGSLRLSCAASGFTVSSYGMSWVRQPPGKGMEWVSGIRGSDGSTYYADSVKGRFTISRDNSRNTLHLQMNSLRAE DTAVYYCAKQGENDGPFDYRGQGTLVTVSS (SEQ ID NO: 42) |
| 314383 | EVQLLESGGGLVQPGGSLRLSCAASGFTVSSYGMSWVRQPPGKGMEWVSGIRGSDGSTYYADSVKGRFTISRDNAKNTLYLQMNSLRAE DTAVYYCAKQGENDGPFDYRGQGTLVTVSS (SEQ ID NO: 43) |
| 314390 | EVQVLESGGGLVQPGGSLRLSCAASGFTVSSYGMSWVRQAPGKGPEWVSGIRGSDGTTYYADSVKGRFTISRDNSRNTLHLQMNSLRAE DTAVYYCAKQGENDGPFDYRGQGTLVTVSS (SEQ ID NO: 44) |
| 314403 | EVQLLESGGGLVQPGGSLRLSCAASGFTISSYGMSWVRQAPGKGPEWVSGIRGSDGTTYYADAVRGRFTISRDISRNILYLQMNSLRAE DTAVYYSCAKQGENDGPFDYRGQGTLVTVSS (SEQ ID NO: 45) |
| 314434 | EVQLLESGGGLVQPGGSLRLSCAASGFTVSSYGMSWVRQPPGKGMEWVSGIRGSDGSTYYADSVKGRFTISRDNAKNTLYLQMNSLRAE DTAVYHCAKQGENDGPFDYRGQGTLVTVSS (SEQ ID NO: 46) |
| 314477 | EVQLLESGGGVVQPGRSLRLSCAASGINFSSYAMSWVRQAPGKGLEWVSAISGDSGNTYYADSVMGRFTISRDNSKNTLYLQMNSLRAE DTAVYHCAKQGENDGPFDYRGQGTLVTVSS (SEQ ID NO: 47) |
| 314480 | EVQLLESGGGVVQPGGSLRLSCAASGFTVSSYGMSWVRQPPGKGMEWVSGIRGSDGSTYYADSVKGRFTISRDKSKNTLYLQMNSLRAE DTAVYHCAKQGENDGPFDYRGQGTLVTVSS (SEQ ID NO: 48) |
| 314486 | EVQLLESGGGLVQPGGSLRLSCAASGFTVSSYGMSWVRQAPGKGPEWVSGIRGSDGSTYYADSVKGRFTISRDNSKNTLYLQMNSLRAE DTAVYHCAKQGENDGPFDYRGQGTLVTVSS (SEQ ID NO: 49) |
| 314488 | EVQLLESGGGLVQPGGSLRLSCAASGFTVSSYGMSWVRQPPGKGMEWVSGIRGSDGSTYYADSVKGRFTISRDNAKNTLYLQMNSLRAE DTAVYHCAKQGENDGPFDYRGQGTLVTVSS (SEQ ID NO: 50) |

Binding to BCMA expressing cell lines

| Column 1 | Column 2 | Column 3 | Column 4 | Column 5 | Column 6 | Column 7 | Column 8 | Column 9 | Column 10 | Column 11 |
|---|---|---|---|---|---|---|---|---|---|---|
| | by Octet | ELISA Binding Ratio (expt signal / diluent only) | | | | | % APRIL | Cell Binding - MFI | | |
| Clone ID | Quant ug/mL | huBCMA ECD | IgG1k | Lambda | HSA | BVPscore | Blocking | RPMI-8226 | NCI-H929 | HDLM2 |
| 308635 | 564.8 | 730.8 | 1.1 | 0.6 | 0.7 | 1.3 | 51.8 | 440.6 | 689.2 | 77.5 |
| 308636 | 588.3 | 716.0 | 1.0 | 0.3 | 0.8 | 1.1 | 90.0 | 330.5 | 283.7 | 79.2 |
| 308806 | 349.9 | 655.6 | 1.2 | 1.3 | 0.7 | 1.0 | 72.0 | 565.8 | 381.0 | 101.6 |
| 308837 | 305.7 | 803.4 | 1.1 | 4.7 | 0.7 | 0.9 | 65.1 | 364.5 | 284.2 | 106.2 |
| 308902 | 688.1 | 868.4 | 1.1 | 1.1 | 0.8 | 1.1 | 95.8 | 722.2 | 669.9 | 101.2 |
| 308912 | 537.4 | 869.7 | 1.1 | 0.9 | 0.9 | 1.0 | 86.1 | 642.7 | 737.0 | 103.7 |
| 308731 | | | | | | | | | 110.9 | |
| 314309 | | | | | | | | | 130.7 | |
| 314322 | | | | | | | | | 162.6 | |
| 314327 | | | | | | | | | 125.5 | |
| 314341 | | | | | | | | | 187.1 | |
| 314344 | | | | | | | | | 146.8 | |
| 314359 | | | | | | | | | 120.0 | |
| 314362 | | | | | | | | | 133.2 | |
| 314364 | | | | | | | | | 121.6 | |
| 314381 | | | | | | | | | 74.0 | |
| 314383 | | | | | | | | | 109.8 | |
| 314390 | | | | | | | | | 85.8 | |
| 314403 | | | | | | | | | 92.2 | |
| 314404 | | | | | | | | | 91.5 | |
| 314407 | | | | | | | | | 70.1 | |
| 314422 | | | | | | | | | 84.1 | |
| 314433 | | | | | | | | | 76.6 | |
| 314434 | | | | | | | | | 99.2 | |
| 314444 | | | | | | | | | 106.4 | |
| 314451 | | | | | | | | | 73.7 | |
| 314453 | | | | | | | | | 85.7 | |
| 314457 | | | | | | | | | 70.4 | |
| 314473 | | | | | | | | | 135.5 | |
| 314474 | | | | | | | | | 172.3 | |
| 314477 | | | | | | | | | 100.7 | |
| 314480 | | | | | | | | | 129.9 | |
| 314481 | | | | | | | | | 229.7 | |
| 314486 | | | | | | | | | 116.8 | |
| 314488 | | | | | | | | | 136.1 | |

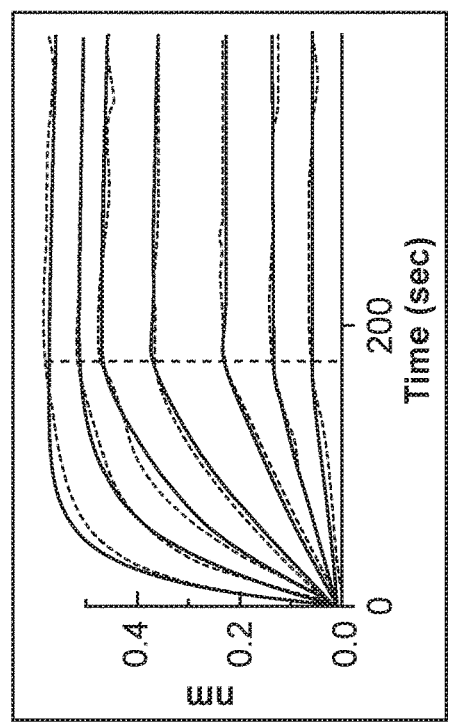
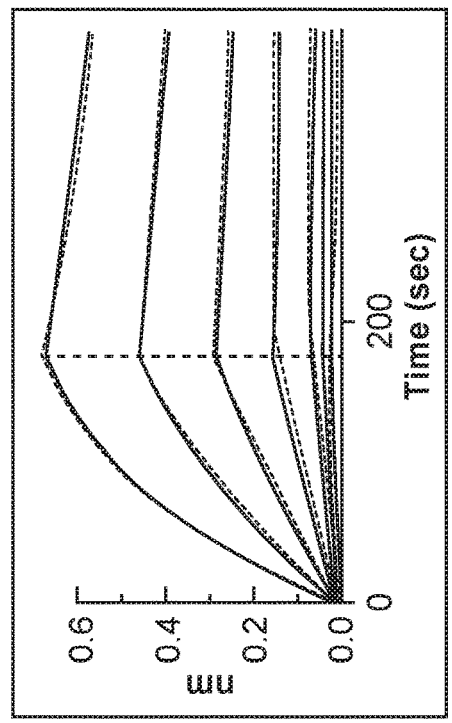
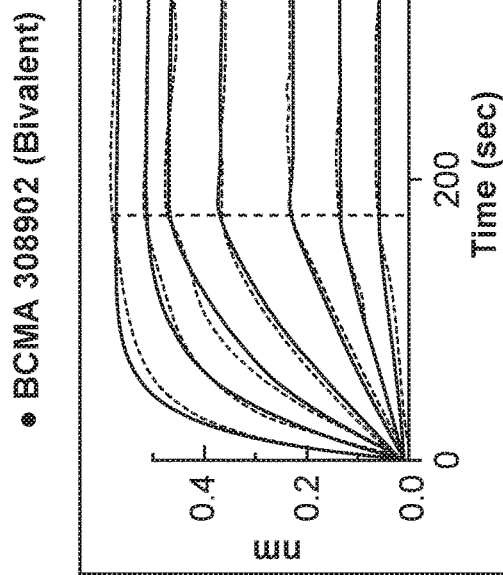
FIG. 4

ANTI-BCMA HEAVY CHAIN-ONLY ANTIBODIES

CROSS REFERENCE TO RELATED APPLICATIONS

This application claims priority benefit of the filing date of U.S. Provisional Patent Application Ser. No. 62/522,295, filed on Jun. 20, 2017, the disclosure of which application is herein incorporated by reference in its entirety.

FIELD OF THE INVENTION

The present invention concerns anti-BCMA heavy chain-only antibodies (UniAb). The invention further concerns methods of making such antibodies, compositions, including pharmaceutical compositions, comprising such antibodies, and their use to treat a B-cell disorder characterized by the expression of BCMA.

BACKGROUND OF THE INVENTION

B-Cell Maturation Antigen (BCMA)

BCMA, also known as tumor necrosis factor superfamily member 17 (TNFRSF17) (UniProt Q02223), is a cell surface receptor exclusively expressed on plasma cells and plasmablasts. BCMA is a receptor for two ligands in the tumor necrosis factor (TNF) superfamily: APRIL (a proliferation-inducing ligand, also known as TNFSF13; TALL-2 and TRDL-1; the high affinity ligand for BCMA) and B cell activation factor (BAFF) (also known as BLyS; TALL-1; THANK; zTNF4; TNFSF20; and D8Ertd387e; the low affinity ligand for BCMA). APRIL and BAFF are growth factors that bind BCMA and promote survival of plasma cells. BCMA is also highly expressed on malignant plasma cells in human multiple myeloma (MM). Antibodies binding to BCMA are described, for example, in Gras et al., 1995, Int. Immunol. 7:1093-1106, WO200124811 and WO200124812. Anti-BCMA antibodies that cross-react with TACI are described in WO2002/066516. Bispecific antibodies against BCMA and CD3 are described, for example, in US 2013/0156769 A1 and US 2015/0376287 A1. An anti-BCMA antibody-MMAE or -MMAF conjugate has been reported to selectively induce killing of multiple myeloma cells (Tai et al., Blood 2014, 123(20): 3128-38). Ali et al., Blood 2016, 128(13):1688-700, have reported that in a clinical trial (#NCT02215967) chimeric antigen receptor (CAR) T cells targeting BCMA resulted in remission of multiple myeloma in human patients.

Heavy Chain-Only Antibodies

In a conventional IgG antibody, the association of the heavy chain and light chain is due in part to a hydrophobic interaction between the light chain constant region and the CH1 constant domain of the heavy chain There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs). The UniAbs of Camelidae (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs lack the first domain of the constant region (CH1) which is present in the genome, but is spliced out during mRNA processing. The absence of the CH1 domain explains the absence of the light chain in the UniAbs, since this domain is the anchoring place for the constant domain of the light chain. Such UniAbs naturally evolved to confer antigen-binding specificity and high affinity by three CDRs from conventional antibodies or fragments thereof (Muyldermans, 2001; J Biotechnol 74:277-302; Revets et al., 2005; Expert Opin Biol Ther 5:111-124). Cartilaginous fish, such as sharks, have also evolved a distinctive type of immunoglobulin, designated as IgNAR, which lacks the light polypeptide chains and is composed entirely by heavy chains IgNAR molecules can be manipulated by molecular engineering to produce the variable domain of a single heavy chain polypeptide (vNARs) (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The ability of heavy chain-only antibodies devoid of light chain to bind antigen was established in the 1960s (Jaton et al. (1968) Biochemistry, 7, 4185-4195). Heavy chain immunoglobulin physically separated from light chain retained 80% of antigen-binding activity relative to the tetrameric antibody. Sitia et al. (1990) Cell, 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, Immunology; 109(1), 93-101; Brüggemann et al., Crit. Rev. Immunol.; 2006, 26(5):377-90; and Zou et al., 2007, J Exp Med; 204(13): 3271-3283. The production of knockout rats via embryo microinjections of zinc-finger nucleases is described in Geurts et al., 2009, Science, 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domains are described, for example, in Iri-Sofia et al., 2011, Experimental Cell Research 317:2630-2641 and Jamnani et al., 2014, Biochim Biophys Acta, 1840:378-386.

SUMMARY OF THE INVENTION

The present invention concerns heavy chain-only antibody binding to human B-Cell Maturation Antigen (BCMA).

In one aspect, the invention concerns a heavy chain-only antibody anti-BCMA antibody comprising a heavy chain variable region comprising:

(a) a CDR1 having two or fewer substitutions in any of the amino acid sequences of SEQ ID NOs: 1 to 7; and/or (b) a CDR2 having two or fewer substitutions in any of the amino acid sequences of SEQ ID NOs: 8 to 11; and/or (c) a CDR3 having two or fewer substitutions in any of the amino acid sequences of SEQ ID NOs: 12 to 15.

In one embodiment, the CDR1, CDR2, and CDR3 sequences are present in a human framework.

In another embodiment, the heavy chain-only antibody further comprises a heavy chain constant region sequence in the absence of a CH1 sequence.

In yet another embodiment, the heavy chain-only antibody comprises:

(a) a CDR1 sequence selected from the group consisting of SEQ ID NOs: 1 to 7; and/or (b) a CDR2 sequence selected from the group consisting of SEQ ID NOs: 8 to 11; and/or (c) a CDR3 sequence selected from the group consisting of SEQ ID NOs: 12 to 15.

In a further embodiment, the heavy chain-only antibody comprises:

(a) a CDR1 sequence selected from the group consisting of SEQ ID NOs: 1 to 7; and (b) a CDR2 sequence selected from the group consisting of SEQ ID NOs: 8 to 11; and (c) a CDR3 sequence selected from the group consisting of SEQ ID NOs: 12 to 15.

In a still further embodiment, the heavy chain only antibody comprises:

(i) a CDR1 sequence of SEQ ID NO: 1, a CDR2 sequence of SEQ ID NO: 8, and a CDR3 sequence of SEQ ID NO: 12; or (ii) a CDR1 sequence of SEQ ID NO: 1, a CDR2 sequence of SEQ ID NO: 8, and a CDR3 sequence of SEQ ID NO: 14; or (iii) a CDR1 sequence of SEQ ID NO: 2, a CDR2 sequence of SEQ ID NO: 9, and a CDR3 sequence of SEQ ID NO: 13; or (iv) a CDR1 sequence of SEQ ID NO: 1, a CDR2 sequence of SEQ ID NO: 8, and a CDR3 sequence of SEQ ID NO: 15.

In a different embodiment, the heavy chain-only antibody comprises a heavy chain variable region having at least 95% sequence identity to any of the sequences of SEQ ID NOs: 16 to 50.

In another embodiment, the heavy chain-only antibody comprises a heavy chain variable region sequence selected from the group consisting of SEQ ID NOs: 16 to 50.

In a further embodiment, the heavy chain-only antibody comprises a heavy chain variable region sequence selected from the group consisting of SEQ ID NOs: 16, 17, 18, 30, 34, and 38.

The invention further concerns a heavy chain-only antibody binding to human B-Cell Maturation Antigen (BCMA) comprising a heavy chain variable region comprising a heavy chain variable comprising (a) a CDR1 sequence of the formula

G F T $X_1$ $X_2$ $X_3$ $X_4$ $X_5$ where
$X_1$ is V, I, or F;
$X_2$ is S or T;
$X_3$ is S or N;
$X_4$ is Y or S;
$X_5$ is G or A;

(b) a CDR2 sequence of the formula

I $X_6$ G $X_7$ $X_8$ $X_9$ $X_{10}$ T where
$X_6$ is R or S;
$X_7$ is S or D;
$X_8$ is D, G, or S;
$X_9$ is G or D;
$X_{10}$ is S, T or N; and (c) a CDR3 sequence of the formula

A K Q G $X_{11}$ N D G P F D $X_{12}$ where
$X_9$ is G or E;
$X_{10}$ is Y or H.

The invention further concerns a heavy chain-only anti-BCMA antibody comprising a heavy chain variable region comprising CDR1, CDR2 and CDR3 sequences in a human VH framework wherein the CDR sequences comprise two or fewer substitutions in a CDR sequence selected from the group consisting of SEQ ID NOs: 1-15.

In one embodiment, the heavy chain-only antibody comprises a heavy chain variable region comprising CDR1, CDR2 and CDR3 sequences in a human VH framework wherein the CDR sequences are selected from the group consisting of SEQ ID NOs: 1-15.

In another embodiment, the heavy chain-only antibody binding to human B-Cell Maturation Antigen (BCMA) comprises a heavy chain variable region comprising (i) a CDR1 sequence of SEQ ID NO: 1, a CDR2 sequence of SEQ ID NO: 8, and a CDR3 sequence of SEQ ID NO: 12; or (ii) a CDR1 sequence of SEQ ID NO: 1, a CDR2 sequence of SEQ ID NO: 8, and a CDR3 sequence of SEQ ID NO: 14; or (iii) a CDR1 sequence of SEQ ID NO: 2, a CDR2 sequence of SEQ ID NO: 9, and a CDR3 sequence of SEQ ID NO: 13; or (iv) a CDR1 sequence of SEQ ID NO: 1, a CDR2 sequence of SEQ ID NO: 8, and a CDR3 sequence of SEQ ID NO: 15, in a human VH framework.

In all embodiments, the heavy chain-only antibody may be multi-specific, such as bispecific.

In certain embodiments, the bispecific heavy chain-only anti-BCMA antibody has binding affinity to two different BCMA proteins, or to two different epitopes on the same BCMA protein.

In other embodiments, the bispecific heavy chain-only anti-BCMA antibody has binding affinity to an effector cell, such as a T-cell antigen.

In further embodiments, the bispecific heavy chain-only anti-BCMA antibody has binding affinity to CD3.

In various embodiments, the multi- or bispecific anti-BCMA antibody can be in a CAR-T format.

In another aspect the invention concerns a pharmaceutical composition comprising a heavy chain-only antibody as hereinabove described.

In yet another aspect, the invention concerns a method for the treatment of a B-cell disorder characterized by the expression of BCMA, the method comprising administering to a subject with such disorder an antibody or a pharmaceutical composition as hereinabove described.

In some embodiments, the B-cell disorder may, for example, be multiple myeloma or systemic lupus erythematosus.

In a further aspect, the invention concerns a polynucleotide encoding an anti-BCMA antibody as described herein.

In a still further aspect, the invention concerns a vector comprising a polynucleotide encoding an anti-BCMA antibody as described herein.

The invention further concerns a cell comprising a vector comprising a polynucleotide encoding an anti-BCMA antibody as described herein.

The invention also concerns a method of producing an antibody as described herein, the method comprising growing a cell (e.g., a host cell) comprising a polynucleotide encoding an anti-BCMA antibody as described herein under conditions permissive for expression of the protein, and isolating the antibody from the cells and/or the cell culture medium. In one embodiment, the method comprises immunizing a UniRat animal with BCMA and identifying BCMA-binding heavy chain antibody sequences.

These and further aspects will be further explained in the rest of the disclosure, including the Examples.

BRIEF DESCRIPTION OF THE DRAWINGS

FIG. 1 shows the CDR1, CDR2 and CDR3 amino acid sequences of 35 heavy chain-only anti-BCMA antibodies of the invention.

FIG. 2 shows the heavy chain variable region sequences of 35 heavy chain-only anti-BCMA antibodies of the invention.

FIG. 3 shows binding of BCMA protein and BCMA-expressing cell lines. Column 1 indicates the clone ID of the heavy chain-only antibody (UniAb) tested. Column 2 indicates the concentration of UniAb expressed in the supernatant. Column 3 indicates the ELISA fold over background signal of human BCMA protein binding. Column 4 indicates the ELISA fold over background signal of human IgG1κ protein binding. Column 5 indicates the ELISA fold over background signal of human lambda protein binding. Column 6 indicates the ELISA fold over background signal of human serum albumin protein binding. Column 7 indicates the ELISA fold over background signal of baculovirus protein binding. Column 8 indicates the percent blocking of the April ligand protein to BCMA protein. Column 9 indicates the mean fluorescent intensity of cell binding to RPMI-8226 cells that express BCMA on the cell surface. Column 10 indicates the mean fluorescent intensity of cell binding to NCI-H929 cells that express BCMA on the cell surface. Column 11 indicates the mean fluorescent intensity of cell binding to HDLM2 cells that do not express BCMA on the cell surface.

FIG. 4 shows the binding affinity of anti-BCMA heavy chain-only antibody 308902 in monovalent and bivalent forms, as measured by BioLayer Interferometry, using an Octet QK384 instrument (Fortebio Inc., Menlo Park, Calif.) in kinetics mode. The binding affinity (Kd) of the monovalent form was 779 pM and the Kd of the bivalent form was 53 pM.

DETAILED DESCRIPTION OF THE PREFERRED EMBODIMENTS

Figure 5:
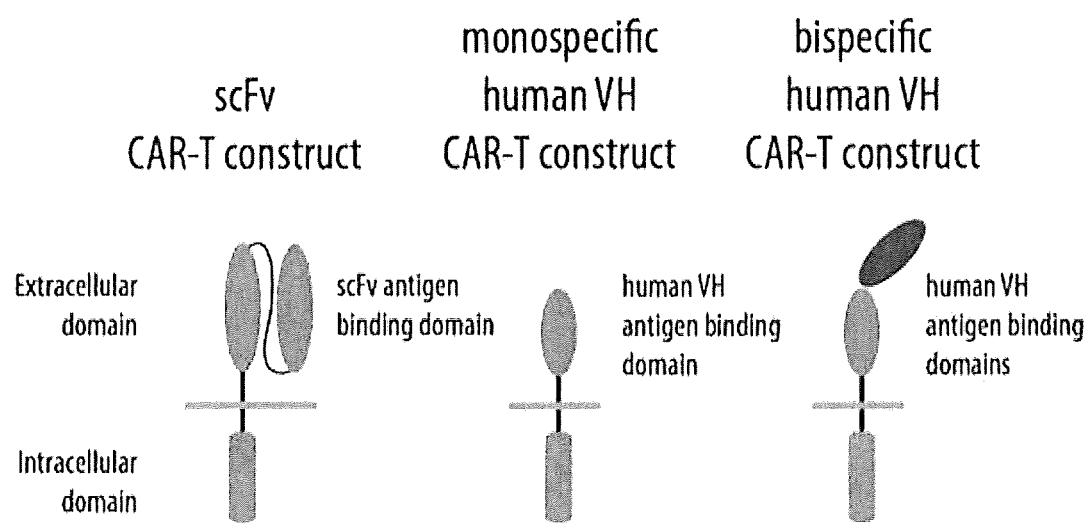
FIG. 5 is a graphic illustration of an scFv CAR-T construct, a monospecific human VH CAR-T construct, and a bispecific human VH CAR-T construct.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The terms "heavy chain-only antibody," "heavy-chain antibody" and "UniAb" are used interchangeably, and refer, in the broadest sense, to antibodies lacking the light chain of a conventional antibody. Since the homodimeric UniAbs lack a light chain and thus a VL domain, the antigen is recognized by one single domain, i.e., the variable domain of the heavy chain of a heavy-chain antibody (VH). The term specifically includes, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs). In one embodiment, the heavy chain-only antibody is composed of the variable region antigen-binding domain composed of framework 1, CDR1, framework 2, CDR2, framework 3, CDR3, and framework 4. In one embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. The heavy chain-only antibody can be in the form of a dimer, in which two heavy chains are disulfide bonded other otherwise, covalently or non-covalently attached with each other. The heavy chain-only antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular IgG1 subtype. In one embodiment, the heavy chain-only antibodies herein are used as a binding (targeting) domain of a chimeric antigen receptor (CAR).

The term "BCMA" as used herein relates to human B cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51).

The term "anti-BCMA heavy chain-only antibody," and "BCMA heavy chain-only antibody" are used herein to refer to a heavy chain-only antibody as hereinabove defined, immunospecifically binding to BCMA.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139., each of which is herein specifically incorporated by reference.

The term "2 (two) or fewer substitutions" in an amino acid sequence is used herein to mean 2 (two), 1 (one) or 0 (zero) substitutions in the reference amino acid sequence.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. "Multi-specific" antibodies specifically include antibodies comprising a combination of different binding entities as well as antibodies comprising more than one of the same binding entity. The terms "multi-specific antibody," multi-specific single chain-only antibody" and "multi-specific UniAb" are used herein in the broadest sense and cover all antibodies with more than one binding specificity.

The term "valent" as used herein refers to a specified number of binding sites in an antibody molecule.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent.

A large variety of methods and protein configurations are known and used for the preparation of bispecific monoclonal antibodies (BsMAB), tri-specific antibodies, and the like.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by VH and/or VL gene segments, D and JH gene segments, or JL gene segments. The variable region may be encoded by rearranged VHDJH, VLDJH, VHJL, or VLJL gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g. the antigen-binding region of a monoclonal antibody or other ligand) to membrane-spanning and intracellular-signaling domains. Typically, the receptor is used to graft the specificity of a monoclonal antibody onto a T cell to create a chimeric antigen receptors (CAR). (J Natl Cancer Inst, 2015; 108(7):dvj439; and Jackson et al., Nature Reviews Clinical Oncology, 2016; 13:370-383.) Representative monospecific and bispecific CAR-T constructs comprising a human VH extracellular binding domain are shown in FIG. 5, in comparison to an scFv CAR-T construct.

By "human idiotype" is meant a polypeptide sequence epitope present on a human antibody in the immunoglobulin heavy and/or light chain variable region. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., Comb Chem High Throughput Screen, 12(8), 791-800, 2009).

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s).

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g. mouse, rat, etc.

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProtP04234), two CDRε chains (SwissProt P07766), and one CD3ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

A "BCMA×CD3 antibody" is a multispecific heavy chain-only antibody, such as a bispecific heavy chain-only antibody, which comprises two different antigen-binding regions, one of which binds specifically to the antigen BCMA and one of which binds specifically to CD3.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-BCMA Antibodies

The present invention provides a family of closely related heavy chain-only antibodies that bind to human BCMA. The antibodies of this family comprise a set of CDR sequences as defined herein and shown in FIG. 1, and are exemplified by the provided heavy chain variable region (VH) sequences of SEQ ID NOs 16 to 50 set forth in FIG. 2. The families of antibodies provide a number of benefits that contribute to utility as clinically therapeutic agent(s). The antibodies include members with a range of binding affinities, allowing the selection of a specific sequence with a desired binding affinity.

A suitable antibody may be selected from those provided herein for development and therapeutic or other use, including, without limitation, use as a bispecific or tri-specific antibody, or part of a CAR-T structure, e.g., as shown in FIG. 5.

Determination of affinity for a candidate protein can be performed using methods known in the art, such as Biacore measurements. Members of the antibody family may have an affinity for BCMA with a $K_d$ of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a BCMA biological activity, including in vitro assays, pre-clinical models, and clinical trials, as well as assessment of potential toxicity.

Members of the antibody family herein are not cross-reactive with the BCMA protein of Cynomolgus macaque but can be engineered to provide cross-reactivity with the BCMA protein of Cynomolgus macaque, or with the BCMA of any other animal species, if desired.

The family of BCMA specific antibodies herein comprises a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 16 to 50. It will be understood by one of skill in the art that the CDR sequences may be in different position if a different framework sequence is selected, although generally the order of the sequences will remain the same.

The CDR1, CDR2, and CDR3 sequences of the anti-BCMA antibodies of the present invention may be encompassed by the following structural formulas, where an X indicates a variable amino acid, which may be specific amino acids as indicated below.

| G F T X1 X2 X3 X4 X5 | CDR1 |
|---|---| where
X1 is V, I, or F;
X2 is S or T;
X3 is S or N;
X4 is Y or S;
X5 is G or A.

In one embodiment, X1 is V or I; X2 is S; X3 is S; X4 is Y; and X5 is G. In another embodiment, CDR1 is selected from the sequence of SEQ ID NOs: 1-6. In yet another embodiment, CDR1 comprises the sequence of SEQ ID NOs 1 or 2. In a further embodiment, CDR1 comprises the sequence GFTVSSYG (SEQ ID NO: 1).

| I X6 G X7 X8 X9 X10 T | CDR2 |
|---|---| where
X6 is R or S;
X7 is S or D;
X8 is D, G, or S;
X9 is G or D;
X10 is S, T or N.

In one embodiment, X6 is D and X7 is G. In another embodiment, X8 is S. In yet another embodiment, X9 is G and X10 is T. In a further embodiment, X9 is G and X10 is S. In a still further embodiment, X9 is G and X10 is T. In another embodiment, CDR2 is selected from the sequence of SEQ ID NOs: 8-11. In yet another embodiment, CDR2 comprises the sequence of SEQ ID NO: 8 or 9. In a particular embodiment, CDR2 comprises the sequence IRGSDGST (SEQ ID NO: 8).

| A K Q G X11 N D G P F D X12 | CDR3 |
|---|---| where
X9 is G or E;
X10 is Y or H.

In one embodiment, X9 is G and X10 is Y. In another embodiment, X9 is G and X10 is H. In another embodiment, X9 is E and X10 is H. In a further embodiment, X9 is E and X10 is Y. In a still further embodiment, CDR3 is selected from the sequence of SEQ ID NOs: 12-15. In another embodiment, CDR3 comprises the sequence of SEQ ID NO: 12, 14 or 15. In yet another embodiment, CDR3 comprises the sequence AKQGENDGPFDH (SEQ ID NO: 14).

Representative CDR1, CDR2, and CDR3 sequences are shown in FIG. 1.

In one embodiment, the anti-BCMA heavy chain-only antibody of the present invention comprises the CDR1 sequence of SEQ ID NO: 1; the CDR2 sequence of SEQ ID NO: 8 and a CDR3 sequence of SEQ ID NO: 12 or 14.

In another embodiment, the anti-BCMA heavy chain-only antibody of the present invention comprises the CDR1 sequence of SEQ ID NO: 2; a CDR2 sequence of SEQ ID NO: 8 or 9; and a CDR3 sequence of SEQ ID NO: 12, 13, 14 or 15.

In a further embodiment, the anti-BCMA heavy chain-only antibody of the present invention comprises the CDR1 sequence of SEQ ID NO:1; the CDR2 sequence of SEQ ID NO: 8; and the CDR3 sequence of SEQ ID NO: 14.

In further embodiments, the anti-BCMA antibody of the present invention comprises any of the heavy chain variable region amino acid sequences of SEQ ID NOs: 16 to 50 (FIG. 2).

In a still further embodiment, the anti-BCMA heavy chain-only antibody of the present invention comprises the heavy chain variable region sequence of SEQ ID NO: 34 (antibody 308902).

In some embodiments, a CDR sequence in the anti-BMA antibodies of the present invention comprises one or two amino acid substitutions relative to a CDR1, CDR2 and/or CDR3 sequence or set of CDR1, CDR2 and CDR3 sequences in any one of SEQ ID NOs:1 to 15 (FIG. 1). In some embodiments said amino acid substitution(s) are one or two of amino acid positions 4-6 of CDR1, and/or one or two of the amino acid positions of 2, 4-7 of CDR2, and/or one or two of the amino acid positions 5 and 12 of CDR3, relative to the formulas provided above. In some embodiment, the single chain-only anti-BCMA antibodies herein will comprise a heavy chain variable region sequence with at least 85% identity, at least 90% identity, at least 95% identity, at least 98% identify, or at least 99% identity to any of the heavy chain variable region sequences shown in FIG. 2.

In some embodiments, bispecific or multispecific antibodies are provided, which may have any of the configurations discussed herein, including, without limitation, a three chain bispecific antibody. Bispecific antibodies comprise at least the heavy chain variable region of an antibody specific for a protein other than BCMA.

Where a protein of the invention is a bispecific antibody, one binding moiety is specific for human BCMA while the other arm may be specific for target cells, tumor associated antigens, targeting antigens, e.g., integrins, etc., pathogen antigens, checkpoint proteins, and the like. Target cells specifically include cancer cells, such as hematologic tumors, e.g., B-cell tumors, as discussed below.

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T-cell bispecific antibodies binding to BCMA, which is selectively expressed on plasma cells (PCs) and multiple myeloma (MM), and CD3 (anti-BCMA×anti-CD3 antibodies). Such antibodies induce potent T-cell mediated killing of cells carrying BCMA, and can be used to treat tumors, in particular hematologic tumors, such as B-cell tumors, as discussed below.

Bispecific antibodies against CD3 and BCMA are described, for example, in WO2007117600, WO2009132058, WO2012066058, WO2012143498, WO2013072406, WO2013072415, and WO2014122144, and in US 20170051068.

Pharmaceutical Compositions

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

Pharmaceutical compositions of the antibodies used in accordance with the present invention are prepared for storage by mixing proteins having the desired degree of purity with optional pharmaceutically acceptable carriers, excipients or stabilizers (see, e.g., Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Anti-BCMA antibody formulations are disclosed, for example, in U.S. Pat. No. 9,034,324. Similar formulations can be used for the proteins of the present invention. Subcutaneous antibody formulations are described, for example, in US 20160355591 and US 20160166689.

Methods of Use

The pharmaceutical compositions herein can be used for the treatment of B-cell related disorders, including B-cell and plasma cell malignancies and autoimmune disorders characterized by the expression or overexpression of BCMA.

Such B-cell related disorders include B-cell and plasma cell malignancies and autoimmune disorders, including, without limitation, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy.

The plasma cell disorders characterized by the expression of BCMA include Multiple Myeloma (MM). MM is a B-cell malignancy characterized by a monoclonal expansion and accumulation of abnormal plasma cells in the bone marrow compartment. Current therapies for MM often cause remissions, but nearly all patients eventually relapse and die. There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating MM in preclinical studies and early clinical trials, consistent clinical efficacy of any monoclonal antibody therapy for MM has not been conclusively demonstrated. There is therefore a great need for new therapies, including immunotherapies for MM (see, e.g., Carpenter et al., Clin Cancer Res 2013, 19(8):2048-2060).

Overexpression or activation of BCMA by its proliferation-inducing ligand, APRIL it known to promote human Multiple Myeloma (MM) progression in vivo. BCMA has also been shown to promote in vivo growth of xenografted MM cells harboring p53 mutation in mice. Since activity of the APRIL/BCMA pathway plays a central role in MM pathogenesis and drug resistance via bidirectional interactions between tumor cells and their supporting bone marrow microenvironment, BCMA has been identified as a target for the treatment of MM. For further details see, e.g., Yu-Tsu Tai et al., Blood 2016; 127(25):3225-3236.

Another B-cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337).

The anti-BCMA heavy chain-only antibodies (UniAb) of the present invention can be used to develop therapeutic agents for the treatment of MM, SLE, and other B-cell disorders or plasma cell disorders characterized by the expression of BCMA, such as those listed above. In particular, the anti-BCMA heavy chain-only antibodies (UniAb) of the present invention are candidates for the treatment of MM, alone or in combination with other MM treatments.

In one embodiment, the antibodies herein can be in the form of heavy chain-only anti-BCMA antibody-CAR structures, i.e., heavy chain-only anti-BCMA antibody-CAR-transduced T cell structures.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but non-human mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage of the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regimen entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents, and formulations thereof, of the invention, and instructions for use. The kits can further contain at least one additional reagent, e.g., a chemotherapeutic drug, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXAMPLES

Example 1

Genetically Engineered Rats Expressing Heavy Chain-Only Antibodies

A 'human—rat' IgH locus was constructed and assembled in several parts. This involved the modification and joining of rat C region genes downstream of human JHs and subsequently, the upstream addition of the human VH6-D-segment region. Two BACs with separate clusters of human VH genes [BAC6 and BAC3] were then co-injected with the BAC termed Georg, encoding the assembled and modified region comprising human VH6, all Ds, all JHs, and modified rat Cγ2a/1/2b (ΔCH1).

Transgenic rats carrying artificial heavy chain immunoglobulin loci in unrearranged configuration were generated. The IgG2a($\Delta C_H 1$), IgG1($\Delta C_H 1$), IgG2b($\Delta C_H 1$) genes lacked the $C_H 1$ segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes. Immunization of transgenic rats resulted in production of high titer serum responses of antigen-specific heavy chain antibodies. These transgenic rats expressing heavy chain antibodies with a human VDJ region were called UniRats.

Example 2

Immunization

Immunization with Recombinant Extracellular Domain of BCMA.

Twelve UniRat animals (6 HC27, 6 HC28) were immunized with recombinant human BCMA protein. The animals were immunized according to standard protocol using a Titermax/Alhydrogel adjuvant. Recombinant extracellular domain of BCMA was purchased from R&D Systems and was diluted with sterile saline and combined with adjuvant. The immunogen was combined with Titermax and Alhydrogel adjuvants. The first immunization (priming) with immunogen in Titermax was administered in the left and right legs. Subsequent boosting immunizations were done in the presence of Alhydrogel and three days before harvest boosts were performed with immunogens in PBS. Serum was collected from rats at the final bleed to determine serum titers.

Serum Titer Results

Binding activity for a single 1:500 serum titer dilution is tested by ELISA against a huBCMA+Fc protein and a cynoBCMA+Fc protein produced in eukaryotic cells and two human BCMA proteins from E. coli and wheat germ, respectively. In addition, serum samples are tested against two off-target proteins, HSA and human IgG1. In addition, serum from all animals is assayed for binding to NCI-H929 cells (BCMA+, lambda−).

Since usually a significant spread of results is observed in serum reactivity levels to NCI-H929 cells (BCMA+, lambda−), the relevance of these results is confirmed by the ELISA binding data generated for a subset of the animals. Positive signal for binding to the cynoBCMA+Fc protein may reflect binding to either the ECD or the Fc portion of the molecule that is also included on the human immunogen. In both assay types, analysis of serum taken from these animals prior to immunization showed no reactivity to the immunogen or off target protein.

Example 3

Gene Assembly, Expression and Binding Assays cDNAs encoding heavy chain only antibodies highly expressed in lymph node cells were selected for gene assembly and cloned into an expression vector. Subsequently, these heavy chain sequences were expressed in HEK cells as UniAb heavy chain only antibodies (CH1 deleted, no light chain).

The results of assays testing the binding of the anti-BCMA heavy chain-only antibodies of the invention are shown in FIG. 3.

Supernatants of 6 antibodies were tested for binding in a standard ELISA assay to a human BCMA. Binding to recombinant BCMA protein was determined by ELISA using human BCMA ECD obtained from Abcam (ab50089). The BCMA ECD protein was used at a concentration of 2 µg/mL to capture UniAbs at 50 ng/mL. Binding of UniAbs was detected with a goat anti-human IgG HRP conjugated antibody (ThermoFisher 31413). All antibodies were diluted in 1×TBS with 0.05% Tween-20 and 1% dry milk powder.

Off-target binding to Baculo Virus Protein Extract (BVP) was conducted by ELISA as above, with the modification of using 1×PBS and 1% dry milk powder for the diluent. BVP extract was obtained from INSERM (Nantes, France). Binding to baculovirus particles (>5× over background in our assay) is thought to indicate low-affinity interactions with human tissues which correlates with reduced half-lives of antibodies in humans and monkeys (Hotzel et al., mAbs 4:6, p 753-760, 2012).

Off-target binding of human IgG1 was assessed by ELISA using the UniAbs to capture human IgG1 kappa followed by detection of the kappa chain with a goat anti-human kappa HRP conjugated antibody (Southern Biotech 2060-05).

Supernatants of the 6 test anti-BCMA antibodies were also tested by flow cytometry for binding to RPMI-8226 cells (BCMA+, lambda+) and supernatants of all 35 anti-BCMA antibodies were and also tested for binding to H929 cells (BCMA+, lambda−). The last column in FIG. 3 shows binding to T-cell-derived Hodgkin's lymphoma (HDLM2) cells, which do not express BCMA on the cell surface.

The samples were measured by flow cytometry using a Guava easyCyte 8HT instrument from EMD Millipore and analyzed using guavaSoft. Bound antibodies were detected with goat anti-human IgG F(ab')2 conjugated to PE (Southern Biotech 2042-09). All antibodies were diluted in PBS with 1% BSA. Positive staining was determined by comparison to staining with a human IgG1 isotype control. The NCI-H929 and RPMI-8226 cell lines are human multiple myeloma lines expressing human BCMA, which were obtained from the American Type Culture Collection (ATCC) and cultured according to ATCC recommendations.

Six UniAbs were also evaluated for the ability to block APRIL (ligand)/BCMA (receptor) binding in a recombinant protein ELISA-style assay. To evaluate blocking of the receptor/ligand interaction between BCMA and APRIL, recombinant human BCMA (Sino Biological 10620-H03H) was directly coated on plates followed by incubation with a dilution series of each UniAb. HA-tagged recombinant APRIL protein (RnD Systems 5860-AP-010) was then incubated with the BCMA/antibody complexes and binding of APRIL to BCMA was detected using a chicken anti-HA antibody conjugated to HRP (Abeam ab1190). An RnD systems anti-BCMA antibody (AF193) was used as a positive control for BCMA/APRIL blocking.

In FIG. 3 column 8 indicates the percent blocking of the April ligand protein to BCMA protein. Column 9 indicates the mean fluorescent intensity of cell binding to RPMI-8226 cells that express BCMA on the cell surface. Column 10 indicates the mean fluorescent intensity of cell binding to NCI-H929 cells that express BCMA on the cell surface. Column 11 indicates the mean fluorescent intensity of cell binding to HDLM2 cells that do not express BCMA on the cell surface.

An additional off-target binding assay was run on intact baculovirus particles (BVPs) though none of the tested UniAbs showed positive binding.

FIG. 4 shows the binding affinity of anti-BCMA heavy chain-only antibody 308902 in monovalent and bivalent forms, as measured by BioLayer Interferometry, using an Octet QK384 instrument (Fortebio Inc., Menlo Park, Calif.) in kinetics mode, essentially as described in Concepcion, J, et al., Comb Chem High Throughput Screen, 12(8), 791-800, 2009. The binding affinity (Kd) of the monovalent form was 779 pM and the Kd of the bivalent form was 53 pM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A heavy chain-only antibody binding to human B-Cell Maturation Antigen (BCMA) comprising a heavy chain variable region comprising a CDR1 sequence of SEQ ID NO: 2, a CDR2 sequence of SEQ ID NO: 9, and a CDR3 sequence of SEQ ID NO: 13.

2. The heavy chain-only antibody of claim 1, wherein said CDR1, CDR2, and CDR3 sequences are present in a human framework.

3. The heavy chain-only antibody of claim 1 further comprising a heavy chain constant region sequence in the absence of a CH1 sequence.

4. The heavy chain-only antibody of claim 1, comprising a heavy chain variable region having at least 95% sequence identity to SEQ ID NO: 30.

5. The heavy chain-only antibody of claim 4 comprising a heavy chain variable region sequence comprising SEQ ID NO: 30.

6. A heavy chain-only antibody binding to human B-Cell Maturation Antigen (BCMA) comprising a heavy chain variable region comprising a CDR1 sequence of SEQ ID NO: 2, a CDR2 sequence of SEQ ID NO: 9, and a CDR3 sequence of SEQ ID NO: 13 in a human VH framework.

7. The heavy chain-only antibody of claim 6, further comprising a heavy chain constant region sequence in the absence of a CH1 sequence.

8. The heavy chain-only antibody of claim 7, which is multi-specific.

9. The heavy chain-only antibody of claim 8, which is bispecific.

10. The heavy chain-only antibody of claim 8, having binding affinity to an effector cell.

11. The heavy chain-only antibody of claim 8, having binding affinity to a T-cell antigen.

12. The heavy chain-only antibody of claim 11, having binding affinity to CD3.

13. A pharmaceutical composition comprising a heavy chain-only antibody of claim 7.

* * * * *

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Val Ser Ser Tyr Gly
1               5

<210> SEQ ID NO 2
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 2

Gly Phe Thr Ile Ser Ser Tyr Gly
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Phe Thr Ile Thr Ser Tyr Gly
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Asn Val Ser Ser Tyr Gly
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Phe Thr Val Ser Asn Tyr Gly
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Phe Thr Phe Ser Ser Ser Ala
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 7

Gly Ile Asn Phe Ser Ser Tyr Ala
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Arg Gly Ser Asp Gly Ser Thr
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Arg Gly Ser Asp Gly Thr Thr
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ile Ser Gly Ser Gly Asp Thr Thr
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Ser Gly Asp Ser Gly Asn Thr
1               5

<210> SEQ ID NO 12
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Lys Gln Gly Gly Asn Asp Gly Pro Phe Asp Tyr
1               5                   10
```

```
<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Lys Gln Gly Gly Asn Asp Gly Pro Phe Asp His
1               5                   10

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Lys Gln Gly Glu Asn Asp Gly Pro Phe Asp His
1               5                   10

<210> SEQ ID NO 15
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ala Lys Gln Gly Glu Asn Asp Gly Pro Phe Asp Tyr
1               5                   10

<210> SEQ ID NO 16
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ala Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110
```

```
Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 19
<211> LENGTH: 119
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Val Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115
```

<210> SEQ ID NO 20
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115
```

<210> SEQ ID NO 21
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 22
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 23
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Val Ser Ser Tyr
            20                  25                  30

Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Leu Glu Ser Gly Gly Gly Leu Val Gln Ala Gly Gly
 1               5                  10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 25
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
 50                  55                  60

Lys Gly Arg Phe Thr Ile Ser Arg Asp Asn Ser Arg Asn Thr Leu Tyr

```
65                  70                  75                  80
Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Leu Glu Ser Gly Gly Asp Leu Val Gln Ser Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Val Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Ser Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110
```

Thr Leu Val Thr Val Ser Ser
        115

<210> SEQ ID NO 28
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Ile Thr Ser Tyr
            20                  25                  30

Gly Met Ser Trp Val Arg Gln Ala Pro Gly Lys Gly Val Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Ser Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 29
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 30
<211> LENGTH: 119

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Val Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Ser Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp His Arg Gly Gln Gly
            100                 105                 110

Thr Leu Val Thr Val Ser Ser
        115

<210> SEQ ID NO 31
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp His Arg Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp His Arg Gly Gln Gly
            100                 105                 110

Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp His Arg Gly Gln Gly
            100                 105                 110

Thr Leu Val Thr Val Ser Ser
        115

<210> SEQ ID NO 34
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

```
Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser
        115
```

<210> SEQ ID NO 35
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

```
Glu Val Gln Leu Leu Glu Ser Gly Gly Gly Leu Val Gln Ala Gly Gly
 1               5                  10                  15

Ser Leu Arg Leu Ser Cys Ala Ala Ser Gly Phe Thr Val Ser Asn Tyr
            20                  25                  30

Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser
        115
```

<210> SEQ ID NO 36
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Pro Glu Trp Val
            35                  40                  45

Ser Gly Ile Arg Gly Ser Asp Gly Thr Thr Tyr Tyr Ala Asp Ser Val
        50                  55                  60
```

Lys Gly Arg Phe Thr Ile Ser Arg Asp Asn Ser Arg Asn Thr Leu His
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser
            115

<210> SEQ ID NO 37
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
                20                  25                  30

Gly Met Ser Trp Val Arg Gln Ala Pro Gly Lys Gly Val Glu Trp Val
            35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp His Arg Gly Gln Gly
            100                 105                 110

Thr Leu Val Thr Val Ser Ser
            115

<210> SEQ ID NO 38
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Val Ser Ser Tyr
                20                  25                  30

Gly Met Ser Trp Val Arg Gln Ala Pro Gly Lys Gly Pro Glu Trp Val
            35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Pro Pro Gly Lys Gly Leu Glu Trp Val
        35                  40                  45

Ser Val Ile Ser Gly Ser Gly Asp Thr Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Asn Ser Arg Asn Thr Leu His
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 41

<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115
```

<210> SEQ ID NO 42
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Arg Asn Thr Leu His
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115
```

<210> SEQ ID NO 43
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Asn Ser Arg Asn Thr Leu His
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 45
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr

```
                    20                  25                  30
Gly Met Ser Trp Val Arg Gln Ala Pro Gly Lys Gly Pro Glu Trp Val
            35                  40                  45

Ser Gly Ile Arg Gly Ser Asp Gly Thr Thr Tyr Tyr Ala Asp Ala Val
        50                  55                  60

Arg Gly Arg Phe Thr Ile Ser Arg Asp Ile Ser Arg Asn Ile Leu Tyr
65                  70                  75                  80

Leu Gln Met Asn Ser Leu Arg Ala Glu Asp Thr Ala Val Tyr Ser Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
            115

<210> SEQ ID NO 46
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Gly Lys Gly Met Glu Trp Val
            35                  40                  45

Ser Gly Ile Arg Gly Ser Asp Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
            115

<210> SEQ ID NO 47
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Val Gln Leu Leu Glu Ser Gly Gly Gly Val Val Gln Pro Gly Arg
1               5                   10                  15

Ser Leu Arg Leu Ser Cys Ala Ala Ser Gly Ile Asn Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Asp Ser Gly Asn Thr Tyr Tyr Ala Asp Ser Val
        50                  55                  60
```

Met Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 48
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
            100                 105                 110

Thr Leu Val Thr Val Ser Ser
        115

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Ile" or "Phe"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Ala"
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 51

```
Gly Phe Thr Val Ser Ser Tyr Gly
1               5

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (4)..(4)
<223> OTHER INFORMATION: /replace="Asp"
<220> FEATURE:
<221> NAME/KEY: VARIANT
<222> LOCATION: (5)..(5)
<223> OTHER INFORMATION: /replace="Gly" or "Ser"
<220> FEATURE:
<221> NAME/KEY: VARIANT
<222> LOCATION: (6)..(6)
<223> OTHER INFORMATION: /replace="Asp"
<220> FEATURE:
<221> NAME/KEY: VARIANT
<222> LOCATION: (7)..(7)
<223> OTHER INFORMATION: /replace="Thr" or "Asn"
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 52

Ile Arg Gly Ser Asp Gly Ser Thr
1               5

<210> SEQ ID NO 53
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Glu"
<220> FEATURE:
<221> NAME/KEY: VARIANT
<222> LOCATION: (12)..(12)
<223> OTHER INFORMATION: /replace="His"
<220> FEATURE:
<221> NAME/KEY: MISC_FEATURE
<222> LOCATION: (1)..(12)
<223> OTHER INFORMATION: /note="Variant residues given in the sequence
      have no preference with respect to those in the annotations
      for variant positions"

<400> SEQUENCE: 53

Ala Lys Gln Gly Gly Asn Asp Gly Pro Phe Asp Tyr
1               5                   10
```